US007833978B2

(12) United States Patent
Chaikof et al.

(10) Patent No.: US 7,833,978 B2
(45) Date of Patent: Nov. 16, 2010

(54) THROMBOMODULIN DERIVATIVES AND CONJUGATES

(75) Inventors: Elliot L. Chaikof, Atlanta, GA (US); Chrystelle S. Cazalis, Pessac (FR); Carolyn A. Haller, Atlanta, GA (US)

(73) Assignee: Emory University, Atlanta, GA (US)

( * ) Notice: Subject to any disclaimer, the term of this patent is extended or adjusted under 35 U.S.C. 154(b) by 345 days.

(21) Appl. No.: 10/598,149

(22) PCT Filed: Feb. 22, 2005

(86) PCT No.: PCT/US2005/005554

§ 371 (c)(1), (2), (4) Date: Apr. 17, 2007

(87) PCT Pub. No.: WO2005/081926

PCT Pub. Date: Sep. 9, 2005

(65) Prior Publication Data

US 2008/0051562 A1 Feb. 28, 2008

Related U.S. Application Data

(60) Provisional application No. 60/546,436, filed on Feb. 20, 2004.

(51) Int. Cl.
*A61K 38/00* (2006.01)

(52) U.S. Cl. ................. 514/12; 514/2; 514/8; 530/350; 530/300

(58) Field of Classification Search ....................... None
See application file for complete search history.

(56) References Cited

U.S. PATENT DOCUMENTS

| | | | | |
|---|---|---|---|---|
| 4,485,045 | A | 11/1984 | Regen | |
| 4,522,803 | A | 6/1985 | Lenk et al. | |
| 4,560,599 | A | 12/1985 | Regen | |
| 4,880,883 | A | 11/1989 | Grasel et al. | |
| 4,906,465 | A | 3/1990 | Chaikof et al. | |
| 5,071,532 | A | 12/1991 | Taillet et al. | |
| 5,108,759 | A | 4/1992 | Ranny | |
| 5,126,140 | A | 6/1992 | Ito et al. | |
| 5,256,770 | A | 10/1993 | Glaser et al. | |
| 5,288,517 | A | 2/1994 | Kanno et al. | |
| 5,399,331 | A | 3/1995 | Loughrey et al. | |
| 5,417,969 | A | 5/1995 | Hsu et al. | |
| 5,429,618 | A | 7/1995 | Keogh | |
| 5,583,102 | A | 12/1996 | Lentz et al. | |
| 5,741,325 | A | 4/1998 | Chaikof et al. | |
| 5,755,788 | A | 5/1998 | Strauss | |
| 5,834,028 | A | 11/1998 | Kunihiro et al. | |
| 5,863,760 | A | 1/1999 | Light et al. | |
| 5,911,942 | A | 6/1999 | Fofonoff et al. | |
| 5,932,462 | A | 8/1999 | Harris et al. | |
| 6,071,532 | A | 6/2000 | Chaikof et al. | |
| 6,171,614 | B1 | 1/2001 | Chaikof et al. | |
| 6,410,057 | B1 | 6/2002 | Kweon-Choi et al. | |
| 6,500,646 | B1 * | 12/2002 | Kuriyama et al. | 435/69.7 |
| 6,565,842 | B1 | 5/2003 | Sojomihardo et al. | |
| 6,583,251 | B1 | 6/2003 | Chaikof et al. | |
| 6,632,791 | B1 | 10/2003 | Light et al. | |
| 6,699,952 | B2 | 3/2004 | Chaikof et al. | |
| 6,936,298 | B2 | 8/2005 | Chaikof et al. | |
| 7,250,168 | B2 * | 7/2007 | Light et al. | 424/192.1 |
| 2004/0063200 | A1 | 4/2004 | Chaikof et al. | |

FOREIGN PATENT DOCUMENTS

| | | |
|---|---|---|
| EP | 0 355 847 | 2/1990 |
| JP | 63236731 | 10/1988 |
| WO | WO 96/21469 | 7/1996 |
| WO | WO 98/16198 | 4/1998 |
| WO | WO 00/00239 | 1/2000 |
| WO | WO 01/78800 | 10/2001 |
| WO | WO 01/80921 | 11/2001 |
| WO | WO 02/09647 | 2/2002 |
| WO | WO 02/055021 | 7/2002 |
| WO | WO 2005/081926 | 9/2005 |

OTHER PUBLICATIONS

Agard et al. (2004) "A Strain-Promoted [3+2] Azde-Alkyne Cycloaddition for Covalent Modification of Biomolecules in Living Systems," *J. Am. Chem. Soc.* 126(46):15046-15047.

Akagawa et al. (2000) "Mechanism of Formation of Elastin Crosslinks," *Connect. Tissue Res.* 41(2):131-141.

Akita et al. (1994) "Effect of FK506 and Ani-CD4 Therapy on Fetal Pig Pancreas Xenografts and Host Lymphoid Cells in NOD/L, CBA, and BALB/c Mice." *Cell Trans.* 3(1):61-73.

Anderson et al. (1994) "Bioactive Silk-Like Protein Polymer Films on Silicon Devices," Alper et al. eds., *Materials Research Society Symp. Proc.*, Pittsburg, PA, 330:171-177.

Andree et al. (1994) "Transport Rate Limited Catalysis on Macroscopic Surfaces; The Activation of Factor X in a Continuous Flow Enzyme Reactor," *Biochem.* 33(14):4368-4374.

Aoi et al. (1994) "Glycopeptide Synthesis by an α-Amino Acid *N*-Carboxyanhydide (NCA) Meth: Ring-Opening Polymerization of a Sugar-Substituted NCA," *Macromol.* 27:875-877.

Aoi et al. (1992) "Architectural Control of Sugar-Containing Polymers by Living Polymerization: Ring-Opening Polymerization of 2-Oxazolines Initiate With Carbohydrate Derivatives," *Macromol.* 25:7073-7075.

Arnander et al (1998) "Influence of Blood Flow and the Effect of Protamine on the Thromboresistant Properties of a Covalently Bonded Heparin Surface," *J. Biomed. Mater. Res.* 22(10):859-868.

(Continued)

*Primary Examiner*—Hope A Robinson
(74) *Attorney, Agent, or Firm*—Greenlee Sullivan P.C.

(57) ABSTRACT

The transmembrane human protein thrombomodulin (TM), as a critical regulator of the protein C pathway, represents the major anticoagulant mechanism that is operative in both normal and injured blood vessels under physiologic conditions in vivo. Compositions and methods are disclosed relating to thrombomodulin derivatives and conjugates, including methods for site-specific pegylation and compositions of a truncated thrombomodulin derivative.

7 Claims, 4 Drawing Sheets

OTHER PUBLICATIONS

Balchander et al. (1990) "Monolayer Transformation by Nucleophilic Substitution: Applications to the Creation of new Monolayer Assemblies," *Langmuir*6(11):1621-1627.
Basmadjian et al. (1997) "Coagulation on Biomaterials in Flowing Blood: Some Theoretical Considerations," *Biomater.* 17(23):1511-1522.
Basmadjian et al. (1983) "Relationships Between Release Rate and Surface Concentration for Heparinized Materials," *J. Biomed. Mater. Res.* 17(3):509-518.
Beyer et al. (1996) "Covalently Attached Polymer Mono- and Multilayers on Silanized Glass Substrates," *Thin Solid Films* 285:825-828.
Bierbaum et al. (1995) "A Near Edge X-Ray Absorption Fine Structure Spectroscopy and X-ray Photoelectron Spectroscopy Study on the Film Properties of Self-Assembled Monolayers of Organosilanes on Oxidized Si(100)," *Langmuir* 11:512-518.
Biessen et al. (1995) "Synthesis of Cluster Galactosides With High Affinity for the Hepatic Asialoglycoprotein Receptor," *J. Med Chem.* 38:1538-1546.
Billy et al. (1995) "Prothrombin Activation by Prothrombinase in a Tubular Flow Reactor," *J. Biol. Chem.* 270(3):1029-1034.
Biro et al. (1994) "Expression and Subcellular Distribution of Basic Fibroblast Growth Factor are Regulated During Migration of Endothelial Cells," *Circ. Res.* 74:485-494.
Bitomsky et akl. (1999) "Docking of Glycosaminoglycans to Heparin-Binding Proteins: Validation for aFGF, bFGF, and Antithrombin and Application to IL-8," *J. Am. Chem. Soc.* 121:3004-3103.
Bjorquist et al. (1997) "Determination of the Kinetic Constants of Tissue Factor/Factor VII/Factor VIIA and Antithrombin/Heparin Using Surface Plasmon Resonance," *Thromb. Res.* 85(3):225-236.
Blezer et al. (1998) "Initiation and Propagation of Blood Coagulation at Artificial Surfaces Studied in Capillary Flow Reactor," *Thromb. Haemost.* 79(2):296-301.
Blezer et al. (1997) "Activation of Blood Coagulation at Heparin-Coated Surfaces," *J. Biomed. Mater. Res.* 37(1):108-113.
Bon et al. (1999) "Amphiphilic Copolymers by Atom Transfer Polymerization with Carbohydrate-Based Initiators and Monomers," *Polym. Prep.* (*Am. Chem. Soc. Div. Polym. Chem.*) 40(2):248-249.
Bourin et al. (1993) "Glycosaminoglycans and the Regulation of Blood Coagulation," *Biochem. J.* 289(2):313-330.
Brittain et al. (1992) "Sickle Erythrocyte Adherence to Large Vessel and Microvascular Endothelium Under Physiologic Flow is Qualitatively Different," *J. Lab. Clin. Med.* 112:538-545.
Broch et al. (1998) "Quantum Molecular Modeling of the Elastinic Tetrapeptide Val-Pro-Gly-Gly," *J. Biomol. Struct. Dyn.* 15:1073-1091.
Brown, D.F.M. (Nov. 2001) "Treatment Options for Deep Venous Thrombosis," *Emerg. Med. Clin. N. Am.* 19(4):913-923.
Brummel et al. (1999) "An Integrated Study of Fibrinogen During Blood Coagulation," *J. Biol. Chem.* 274(32)22862-22870.
Buller et al. (1999) "Primary Stenting Versus Balloon Angioplasty in Occluded Coronary Arteries," *Circ.* 100(3):236-242.
Bundgeerd, H. (1991) "Design and Application of Prodrugs," in *A Textbook of Drug Design and Application of Prodrugs*, Krosgaard-Larsen et al. eds., pp. 113-191.
Bundgaard, H. (1992) "(C) Means to Enhance Penetration, (1) Prodrugs as a Means to Improve Delivery of Peptide Drugs," *Adv. Drug Dell. Rev.* 8:1-38.
Byun et al. (196) "Binding of Antithrombin III and Thrombin to Immobilize Heparin Under Flow Conditions," *Biotechnol. Prog.* 12(2):217-225.
Byun et al. (1996) "Mechanism of Thrombin Inactivation by Immobilized Heparin," *J. Biomed. Mater. Res.* 30:423-427.
Cai et al: (1993) "A Solid-State N.M.R. Study of Microphase Structure and Segmental Dynamics of Poly(Styrene-*b*-methylphenylsiloxane) Diblock Copolymers," *Polymer* 34:267-276.
Calistri-Yeh et al. (1996) "Thermal Stability of Self-Assembled Monolayers from Alkylchlorosilanes," *Langmuir* 12:2747.
Campbell et al. (1994) "Biocompatibie Surfaces Using Methacryloylphosphorylcholine Laurylmethacrylate Copolymer," *ASAIO J.* 40(3):M853-M857.
Cao et al. (1997) "Sequence of Abductin, The Mollyscan "Rubber" Protein," *Vurr. Biol.* 7:R677-R678.
Cazalis et al. (2004) "Site-Specific PEGylation of a Truncated Thrombomodulin Derivative," *Polymer Mater. Sci. Eng.* 227:198-199.
Cazalis et al. (2004) "C-Terminal Site Specific Pegylation of Truncated Thrombomodulin Mutant with Retention of Full Bioactivity," *Bioconjug. Chem.* 15:1005-1009.
Chaikof et al. (1996) "Biomaterials that Imitate Cell Microenvironments," *Chemtech* 26:17-24.
Chaikof et al. (1992) "PEO Enhancement of Platelet Deposition, Fibrinogen Deposition, and Complement C3 Activation," *J. Biomed. Mater. Res.* 26:1163-1168.
Chan et al. (2006) "*Homo sapiens* Thrombomodulin," NCBI Accession No. NM_000361.
Chang et al. (1989) "Nuclear Overhauser Effect and Computational Characterization of the β-Spiral of the Polypentapeptide of Elastin," *J. Biomol. Struct. Dyn.* 6(5);851-858.
Chang et al. (1988) "Molecular Dynamics Calculations on Relaxed and Extended States of the Polypentapeptide of Elastin," *Chem. Phys. Lett.* 147:395-400.
Chapman et al. (1993) "Biomembranes and New Hemocompatible Materials," *Langmuir* 9:39-45.
Chen et al. (1997) "Phosphorylcholine Coating of ePTFE Grafts Reduces Neointimal Hyperplasia in Canine Model" *Ann. Vasc. Surg.* 11(1):74-79.
Chen et al. (1996) "Studies on the Synthesis and Properties of Novel Phospholipid Analogous Polymers," *J. App. Polym. Sci.* 60:455-464.
Cheung et al. (1994) "Molecular Self-Assembly of Conducting Polymers," *Thin Solid Films*, 244;985-989.
Chon et al. (1999) "Cytomimetic Biomaterials, 3. Preparation and Transport Studies of an Alginate/Amphiphilic Copolymer/Polymerized Phospholipid Film," *J. Biomater. Sci. Polym. Ed.* 10:95-107.
Chon et al. (1998) "α4β1 and α5β1 Control Cell Migration on Fibronectin by Differentially Regulating Cell Speed and Motile Cell Phenotype," *Ann. Biomed. Eng.* 26:1091-1101.
Chon et al. (1997) "Role of Fibronectin and Sulfated Proteoglycans in Endothelial Cell Migration on a Cultures Smooth Muscle Layer," *J. Surg. Res.* 72:53-59.
Christianson et al. (1993) "Adoptive Transfer of Diabetes into Immunodeficient NOD-*scid/scid* Mice: Relative Contributions of $CD4^+$ and $CD8^+$ T-Cells from Diabetic Versus Prediabetic NOD. NON-*Thy*-$1^+$ Donors," *Diabetes* 42:44-55.
Cima et al. (1995) "Network Structures of Radiation-Cross-Linked Star Polymer Gels," *Macromol.* 28:6787-6794.
Clarke et al. (1993) "The Short Loop Between Epidermal Growth Factor-Like Domain-4 and Domain-5 is Critical for Human Thrombomodulin Function," *J. Biol. Chem.* 268:6309-6315.
Clowes et al. (1986) "Mechanisms of Arterial Graft Failure. II. Chronic Endothelial and Smooth Muscie Cell Proliferation in Healing Polytetrafluorothylene Prostheses," *J. Vasc. Surg.* 3:877-884.
Clowes et al. (1985) "Mechanisms of Arterial Graft Failure. I. Role of Cellular Proliferation in Early Healing of PTFE Prostheses," *Am. J. Pathol.* 118(1):43-54.
Clowes et al. (1977) "Suppression by Heparin of Smooth Muscle Cell Proliferation in Injured Arteries," *Nature*:625-626.
Colton et al. (1992) "The Engineering of Xenogenetic Islet Transplantation by Immunoisolation," *Diab. Butr: Metabol.* 5:145-149.
Colton et el. (1991) "Bioengineering in the Development of the Hybrid Artificial Pancreas I," *Biochem. Eng.* 113:152-170.
Contino et al. (1994) "Use of an Oriented Transmembrane Protein to Probe the Assembly of a Supported Phospholipid Bilayer," *Biophys. J.* 67:1113-1116.
Conway et al. (Jan. 1997) "The Amino Terminal Lactin-Like Domain of Thrinbifulin is Required for Constitutive Endocytosis," *Blood* 89(2):652-661.
Crooks et al. (1990) "Microencapsulation of Mammalian Cells in HEMA_MMA Copolymer: Effects on Capsule Morphology and Permeability," *J. Biomed. Mater. Res.* 24:1241-1262.

Cruise et al. (1998) "A Sensitivity Study of the Key Parameters in the Interfacial Photopolymerizaion of Poly(Ethylene Glycol) Diacrylate Upon Porcine Islets," *Biotechnol. Bioeng*. 57:655-5-665.
Daugherty et al. (1999) "A Fluorescence Assay for Leucine Zipper Dimerization: Avoiding Unintended Consequences of Fluorophore Attachment," *J. Am. Chem. Soc*. 121:4325-4333.
Dautzenberg et al. (1996) "Polyelectrolyte Complex Formation at the Interface of Solutions," *Polym. Sci*. 101:149-156.
Debelle et al. (1999) "Elastin: Molecular Description and Function," *Int. J. Biochem. Cell Biol*. 31:261-272.
Decher, G. (1997) Fuzzy Nanoassemblies: Toward Layered Polymeric Multicomposites, *Science* 277:1232-1237.
Defrees et al. (1996) "Sialyl Lewis X Liposomes as a Multivalent Ligand and Inhibitor of E-Selectin Mediated Cellular Adhesion," *J. Am. Chem. Soc*. 118:6101-6104.
Deming, T.J. (1999) "Mussel Bysus and Biomolecular Materials," *Curr. Opin. Chem. Biol*. 3:100-105.
Dixon, W.T. (1982) "Spinning-Sideband-Free and Spinning Sideband-Only NMR pectra in Spinning Samples," *J. Chem. Phys*. 77:1800-1809.
Dixon, W.T. (1982) "Total Suppression of Sidebands in CPMAS C-13 NMR," *J. Magn. Reson*. 49:341-345.
Dluhy, R.A. (1986) "Quantitative External Reflection Infrared Spectroscopic Analysis of Insoluble Monolayers Spread at the Air-Water Interface," *J. Phys. Chem*. 90:1373-1379.
Dodson et al. (1993) "Molecular Recognition in Insulin Assembly," *Biochem. Soc. Trans*. 21:609-614.
Doshi et al. (1995) "Electospining Process and Applications of Electrospun Fibers," *J. Electrostatics* 35:151-160.
Eaton, D.F. "Dye Sensitized Photo Polymerization," *Advances in Photochem*. 13:427-487.
Egger et al. (1992) "Solid State NMR Investigation of Cationic Polymerized Epoxy Resins," *J. Appl. Poly. Sci*. 44;289-295.
Einaga et al. (1999) "Photofunctional Vesicles Containing Prussian Blue and Azobenzene," *J. Am. Chem. Soc*. 121:3745-3750.
Eitzman et al. (1994) "Heparin Neutralization by Platelet-Rich Thrombi," *Circulation* 89(4):1523-1529.
Ejaz et al. (2000) "Controlled Grafting of a Well Defined Glycopolmer on a Solid Surface by Surface-Initiated Atom Transfer Radical Polymerization," *Macromol*. 33:2870-2874.
Elbert et al. (1999) "Thin Polymer Layers Formed by Polyelectrolyte Multilayer Techniques on Biological Surfaces," *Langmuir* 15:5355-5362.
Elender et al. (1996) "Functionalization of Si/$SiO_2$ and Glass Surfaces with Ultrathin Dextran Films and Deposition of Lipid Bilayers," *E. Biosensors Bioelectronics* 11:565-577.
Elliott et al. (2000) "Maleimide-Functionalized Lipids that Anchor Polypeptides to Lipid Bilayers and Membranes," *Bioconjug. Chem*. 11:832-841.
Esmon et al. (1999) "Regulation and Functions of the Protein C Anticoagulant Pathway," *Haematologica* 84(4):363-368.
Esmon et al. (1997) "The Protein C Pathway: New Insights," *Thromb. Haemost*. 78(1):70-74.
Esmon, C.T. (1995) "Thrombomodulin as a Model of Molecular Mechanisms that Modulate Protease Specificity and Function at the Vessel Surface," *FASEB J*. 9(10):946-955.
Esmon et al. (1982) "Isolation of a Membrane-Bound Cofactor for Thrombin-Catalyzed Activation of Protein-C," *J. Biol. Chem*. 257:859-864.
Esmon, C.T. (1992) "The Protein C Anticoagulant Pathway," *Arteriosclerosis and Thrombosis* 12:135-145.
Esmon et al. (1981) "Identification of an Endothelial Cell Cofactor for Thrombin-Catalyzed Activation of Protein C," *Proc. Nat. Acad. Sci. USA* 78(4):2249-2252.
Esmon et al. (1983) "Proteolytic Formation and Properties of γCarboxygluamic Acid-Domainless Protein C." *J. Biol. Chem*. 258(9):5548-5553.
Esmon et al. (1983) "Thrombomodulin Blocks the Ability of Thrombin to Activate Platelets," *J. Biol. Chem*. 258(20):12238-12242.
Espana et al. (1991) "In Vivo and In Vitro Complexes of Activated Protein C with Two Inhibitors in Baboons," *Blood* 77(8):1116-1120.
Faham et al. (1996) "Heparin Structure and Interactions with Basic Fibroblast Growth Factor," *Science* 271:1116-1120.
Feingold et al. (1986) "Coagulation Assays and Platelet Aggregation Patterns in Human, Baboon, and Canine Blood," *Am. J. Vet. Res*. 47:2197-2199.
Feng et al. (2000) "Reconstitution of Thrombomodulin into Polymerizable Phospholipid Vesicles," *Polymer Preprints* 41(2)1653-1654.
Feng et al. (2002) "Functional Reconstitution of Thrombomodulin within a Substrate-Supported Membrane-Mimetic Polymer Film," *Langmuir* 18:9907-9913.
Flitsch, S.L. (Dec. 2000) "Chemical and Enzymatic Synthesis of Glycopolymers," *Curr. Opin. Chem. Biol*. 4(6):619-625.
Florin et al. (1993) "Painted Supported Lipid Membranes," *Biophys. J*. 64:375-383.
Fong et al. (1999) "Beaded Nanofibers Formed During Electrospinning," *Polymer* 40:4585-4592.
Foster et al. (1973) "Isolation and Amino Acid Sequences of Tropoelastin Peptides," *J. Biol. Chem*. 24:2876-2879.
Frank et al. (1991) "The Role of Complement in Inflammation and Phagocytosis," *Immunol. Today* 12:322-326.
Franzblau et al. (1977) "Role of Crosslinking in Fiber Formation," *Adv. Exp. Med. Biol*. 79:313-327.
Galvin et al. (1987) "Reconstitution of Rabbit Thrombomodulin into Phospholipid Vesicles," *J. Biol. Chem*. 262(5):2199-2205.
Gemmell et al. (1990) "The Effects of Shear Rate on the Enzymatic Activity of the Tissue Factor-Factor VIIa Complex," *Microvasc. Res*. 40(30):327-340.
Gemmell et al. (1990) "Utilization of a Continuous Flow Reactor to Study the Lipoprotein-Associated Coagulation Inhibitor (LACI) that Inhibits Tissue Factor," *Blood* 76(11):2266-2271.
Gentry et al. (1995) "Surface-Mediated Enzymatic Reactions: Simulations of Tissue Factor Activation of Factor X on a Lipid Surface," *Biophys. J*. 69(2):362-271.
Gerling et al. (1994) "Multiple Low-Dose Sreptozocin-Induced Diabetes in NOD-*scid/scid* Mice in the Absence of Functional Lymphcytes," *Diabetes* 43:433-440.
Gill et al. (1994) "$CD4^+$ T Cells are Both Necessary and Sufficient for Isle Xenograft Rejection," *Trans. Proc*. 26:1203.
Gir et al. (1996) "A Numerical Analysis of Factor X Activation in the Presence of Tissue Factor/Factor VIIa Complex in a Flow Reactor," *Ann. Biomed. Eng*. 24(3):394-399.
Glaser et al. (1992) "Oxidation of a Specific Methionine in Thrombomodulin by Activated Neutrophil Products Blocs Cofactor Activity. A Potential Rapid Mechanism for Modulation of Coagulation," *J. Clin. Invest*. 90:2565-2573.
Gnanou et al. (1998) "Synthesis of Star Shaped Poly(Ethylene Oxide)," *Makromol. Chem*. 189:2885-2892.
Goeden-Wood et al. (2002) "Improved Assembly of Multimeric Genes for the Biosynthetic Production of Protein Polymers," *Biomacromol*. 3(4):874-879.
Golden et al. (1990) "Healing of Polytetrafluoroethylene Arterial Grafts is Influenced by Graft Porosity," *J. Vasc. Surg*. 11(6):838-844.
Goldsmith et al. (1986) "Rheological Aspects of Thrombosis and Haemostasis: Basic Principles and Applications," *Thromb. Haemostas*. 55(3):415-435.
Goodson et al. (1990) "Site-Directed Pegylation of Recombinant Interleukin-2 at its Glycosylation Site," *Bio-Technology* 8:343-346.
Goosen et al. (1985) "Optimization of Microencapsulation Parameters: Semipermeable Microcapsules as a Bioartificial Pancreas," *Biotech. Bioeng*. 27:146-150.
Goosen et al. (1980) "Inactivation of Throbin by Antithrombin III on a Heperinized Biomaterial," *Thromb. Res*. 20(5-6): 543-554.
Grande et al. (2001) "Glycosaminoglycan Mimetic Biomaterials. 2. Alkene- and Acrylate-Derived Glycopolymers Via Cyanoxyl-Mediated Free-Radical Polymerization," *Macromol*. 34:1640-1646.
Grande et al. (2000) "Glcosaminoglycan Mimetc Biomaterials. 1. Nonsulfated and Sulfated Glycopolymers by Cyanoxyl-Mediated Free-Radical Polymerization," *Macromol* 33:1123-1125.
Grande et al. (2000) "Synthesis of Non-Sulfated and Sulfated Glycopolymers," *Polymer Preprints* 41(1):1000-1001.
Gray et al. (1973) "Molecular Model for Elastin Structure and Function," *Nature* 246:461-466.

Gruber et al. (1991) "Antithrombotic Effects of Combining Activated Protein C and Urokinase in Nonhuman Primates," *Circulation* 84(6):2454-2462.
Gruber et al. (1990) "Inhibition of Thrombus Formation by Activated Recombinant Protein C in a Primate Model of Arterial Thrombosis," *Circulation* 82(2):578-585.
Gruber et al. (1989) "Inhibition of Platelet Dependent Thrombus Formation by Human Activated Protein C in a Primate Model," *Blood* 73(3):639-742.
Haj Mohammadi et al. (2003) "Normal Levels of Anticoagulant Heparan Sulfate are Not Essential for Normal Hemostasis," *J. Clin. Invest.* 111:989-999.
Hall et al. (1998) "Factor Xa Generation at the Surface of Cultured Rat Vascular Smooth Muscle Cells in an In Vitro Flow System," *J. Biomech. Eng.* 120(4):484-490.
Hall et al. (1989) "Biomembranes as Models for Polymer Surfaces," *Biomater.* 10(4):219-224.
Hallé et al. (1993) "Protection of Islets of Langerhans from Antibodies by Microencapsulation with Alginate-poly-L-Lysine Membranes," *Transplant.* 44:350-354.
Han et al. (2001) "Studies of a Novel Human Thrombomodulin Immobilized Substrate: Surface, Characterization, and Anticoagulation Activity Evaluation," *J. Biomater. Sci. Polymer ed.* 12:1075-1089.
Hanson et al. (1998) "Blood Flow and Antihrombotic Drug Effects," *Am. Heart J.* 135(5 Pt 2 SU) S132-S145.
Hanson et al. (1993) "Antithrombotic Effects of Thrombin-Induced Activation of Endogenous Protein C in Primates," *J. Clin. Invest.* 92:2003-2012.
Hanson et al. (1991) "Effects of Angiotensin Converting Enzyme Inhibition with Cilazapril on Intimal Hyperplasia in Inured Arteries ad Vascular Grafts in the Baboon," *Hypertension* 18(4):II-70-II-76.
Hanson et al. (1985) "Platelet Interactions with Dacron Vascular Grafts; A Model of Acute Thrombosis in Baboons," *Arteriosclerosis* 5(6):595-603.
Harker et al. (Apr. 2000) "Effects of Megakaryocyte Growth and Development Factor on Platelet Production, Platelet Life Span, and Platelet Function in Healthy Human Volunteers," *Blood* 95(8):2514-2522.
Hasegawa et al. (1995) "Quantitative Analysis of Uniaxial Molecular Orientation in Langmuir-Blodgett Films by Infrared Relection Spectroscopy," *Langmuir* 11:1236-1243.
Haskins et al. (1990) "Acceleration of Diabetes in Young NOD Mice with $CD4^+$Islet-Specific T Cell Clone," *Science* 249:1433-1436.
Haude et al. (2003) "Heparin-Coated Stent Placement for the Treatment of Stnosis in Small Coronary Arteries of Symptomatic Patients," *Circulation* 107:1265-1270.
Hayashi et al. (1999) "Hypotheses that Correlate the Sequence, Structure, and Mechanical Properties of Spider Silk Proteins," *Int. J. Biol. Macromol.* 24:271-275.
Hayashi et al. (1998) "Evidence from Flagelliform Silk cDNA for the Structural Basis of Elasticity and Modular Nature of Spider Silks," *J. Mol. Biol.* 275:773-784.
Hayword et al. (1986) "Biomembranes as Models for Polymer Surfaces," *Biomater.* 7:252-258.
Hayword et al. (1984) "Biomembrane Surfaces as Models for Polymer Design: The Potential for Haemoompatibility," *Biomater.* 5:135-142.
Hayzer et al. (1999) "cDNAs Encoding the Baboon Thrombin Receptor Indicate a Primate Transcription Start Site Upstream of Putative Sites Reported for the Human Gene," *Thromb. Res.* 98:195-201.
Hayzer et al. (1993) "Characterization of a cDNA Encoding the β-Chain of Baboon Receptor Glycoprotein BPib," *Gene* 127:271-272.
He et al. (1999) "Site-Directed Polyethylene Glycol Modification of Trichosanthin: Effects on its Biological Activities, Pharmacokinetics, and Antigenicity," *Life Sci.* 64:1163-1175.
Hebert et al. (1992) "A New Reagent for the Removal of the 4-Methozybenzyl Ether: Application to the Synthesis of Unusual Macrocyclic and Bolaform Phosphatidylcholines," *J. Org. Chem.* 57:1777-1783.
Helm et al. (1991) "Measurement of Ligand-Receptor Interactions," *Proc. Nat. Acad. Sci. USA* 88:8169-8173.
Hergenrother et al. (2000) "Small-Molecule Microarrays: Covalent Attachment and Screening of Alcohol-Containing Small Molecules on Glass Slides," *J. Am. Chem. Soc.* 122:7849-7850.
Heroguez et al. (1997) "Novel Amphiphilic Architectures by Ring-Opening Metathesis Polymerization of Macromonomers," *Macromol.* 30:4791-4798.
Huang et al. (2000) "Generation of Synthetic Elastin-Mimetic Small Diameter Fibers and Fiber Networks," *Macromol.* 33:2989-2997.
Hubbell et al. (1991) "Endothelial Cell-Selective Materials for Tissue Engineering in the Vascular Graft Via a New Receptor," *Bio/Technol.* 9:568-572.
Hudson et al. (1997) "The Spinning of Silk-Like Proteins into Fibers," In; *Protein Based Materials*, McGrath et al., Boston, pp. 313-337.
Ishihara, K. (1997) "Novel Polymeric Materials for Obtaining Blood-Compatible Surfaces," *TRIP* 5(12):401-407.
Ishihara et al. (1995) "Synthesis of Phospholipid Polymers Having a Urethane Bond in the Side Chain as Coating Material on Segmented Polyurethane and Their Platelet Adhesion-Resistant Properties," *Biomater.* 16:873-879.
Ishihara et al. (1994) "Haemocompatibility on Graft Copolymers Composed of Poly(2-Methacryloyloxyethyl Phosphorylcholine) Side Chain and Poly(*n*-butyl Methacrylate) Backbone," *J. Biomed. Mater. Res.* 28:225-232.
Ishihara et al. (1992) "Hemocompatibility of Human Whole Blood Polymers with a Phospholipid Polar Group and Its Mechanism," *J. Biomed. Mater. Res.* 26:1543-1552.
Ishiara et al. (1990) "Reduced Thrombogeniciy of Polymers Having Phospholipid Polar Groups," *J. Biomed. Mater. Res.* 24:1069-1077.
Ito et al. (1992)"Cell Growth Factor Immobilized Materials," In; *Synthesis of Biocomposite Materials: Chemical ad Biological Modified Natural Polymers*, Imanishi, Y. ed., Section 5.2, Boca Raton, Fl, CRC Press, pp. 285-310, 314.
Jackson et al. (1991) "Glycosaminoglycans: Molecular Properties, Protein Interactions, and Role in Physiological Processes," *Physiol. Rev.* 71(2):481-539.
Janeway et al. (1994) "Signals and Signs for Lymphocyte Responses," *Cell.* 76:275-285.
Jarpe et al. (1990) "Flow Cytometric Enumeration of Mononuclear Cell Populations Infiltrating the Islets of Langerhans in Prediabetic NOD Mice: Development of Model of Autoimmune Insulinitis for Type I Diabetes," *Regional Immunol.* 3:305-317.
Kagan et al. (1980) "Repeat Polypeptide Models of Eastin as Substrates for Lysyl Oxidase," *J. Biol. Chem.* 255:3656-3659.
Kalafatis et al. (1997) "The Regulation of Clotting Factors," *Crit. Rev. Eukaryot. Gene Expr.* 7:241-280.
Kalafatis et al. (1996) "Regulation and Regulatory Role of γ-Carboxyglutamic Acid Containing Clotting Factors," *Crit. Rev. Eukaryotic Gene Expression* 6(1):87-101.
Karpusas et al. (1997) "The Crystal Structure of Human Interferon Beta at 2.2-A Resolution," *Proc. Nat. Acad. Sci. USA* 94:11813-11818.
Katre, N.V. (1993) "The Conjugation of Proteins with Polyethylene Glycol and Other Polymers. Altering Properties of Proteins to Enhance Their Therapeutic Potential," *Adv. Drug Deliv. Rev.* 10:91-114.
Kawamoto et al. (1992) "Reconstituted Collagen is Not Capable of Activating XII but Causes Intrinsic Coagulation by Activating Platelets," *Blood. Coagulation Fibrinolysis* 3(4):371-379.
Ke et al. (1995) "Ovalbumin Injected with Complete Freund's Adjuvant timulates Cytolyic Responses," *Eur. J. Immunol.* 1995:549-553.
Khaled et al. (1976) "Proton Magnetic Resonance and Conformational Energy Calculations of Repeat Peptides of Tropoelastin: The Tetrapeptide," *J. Am. Chem. Soc.* 98:7547-7553.
Kiick et al. 2002 "Incorporation of Azides into recombinant Proteins for Chemoselective Modification by the Stadinger Ligation," *Proc. Nat. Acad. Sci. USA* 99:19-24.
Kim et al. (2000)"The Influence of Tiered Layers of Surface-Grafted Ply(ethylene Glycol) on Receptor-Ligand-Mediated Adhesion Between Phospholipid Monolayer-Stabilized Microbubbles and Coated Glass Beads," *Langmuir* 16:2808-2817.

Kim et al. (Feb. 2001) "Characterizing Structural Changes in Point-Bonded Nonwoven Fabrics During Load-Deformation Experiments," *Textile Res. J.* 71(2):157-164.
Kimura et al. (1992) "High-Resolution Solid-State $^{13}C$ Nuclear Magnetic Resonance Study of the Combined Process of $^{1}H$ Spin Diffusion and $^{1}H$ Spin-Lattice Relaxation in Semicrystalline Polymers," *Polymer* 33(3):493-497.
King et al. (1987) "Alginate-Polylysine Microcapsules of Controlled Membrane Molecular Weight Cutoff for Mammalian Cell Culture Engineering," *Bioech. Prog.* 3:231-240.
Kishida et al. (1995) "In Vivo and Ex Vivo Evaluation of the Antthrombogenicity of Human Thrombomodulin Immobilized Biomaterials," *ASAIO J.* 41(3):M369-374.
Kishida et al. (1994) "Immobilization of Human Thrombomodulin on Biomaterials-Evaluation of the Activity of Immobilized Human Thrombomodulin," *Biomat.* 15(14):1170-1174.
Kishida et al. (1994) "Immobilization of Human Thrombomodulin onto Poly(Ether Urethane urea) for Developing Antithrombogenic Blood-Contacting Materials," *Biomat.* 15(10):848-852.
Kishida et al. (1994) "Immobilization of Human Thrombomodulin onto Biomaterials," *ASAIO J.*40(3):M840-M845.
Kobayashi et al. (1974) "Theory of the Kinetics of Reactions Catalyzed by Enzymes Attached to Membranes," *Biotech. Bioeng.* 16(1):77-97.
Kobayashi et al. (1974) "Theory of the Kinetics of Reactions Catalyzed by Enzymes Attached to the Interior Surfaces of Tubes," *Biotech. Bioeng.* 16(1):99-118.
Kogan, T.P. (1992) "The Synthesis of Substituted Methoxy-Poly(Ethylene Glycol) Derivatives Suitable for Selective Protein Modification," *Synth. Commun.* 22:2417-2424.
Kohler et al. (1996) "Platelet Adhesion to Novel Phospholipid Materials: Modified Phosphatidylcholine Covalently Immobilized to Silica, Polypropylene, and PTFE Materials," *J. Biomed. Mater. Res.* 32:237-242.
Kojima et al. (1991) "Interaction Between Phospholipids and Biocompatible Polymers Containing a Phosphorylcholine Moiety," *Biomater.* 12:121-124.
Korbutt et al. (1996) "Large Scale Isolation, Growth, and Function of Porcine Neonatal Islet Cells," *J. Clin. Invest.* 97(9):2119-2129.
Korbutt et al. (1995) "Porcine Islet Cell Antigens are Recognized by Xenoreactive Natural Human Antibodies of Both IgG and IgM Subtypes," *Transplant. Proc.* 28:821-823.
Korbutt et al. (1995) "Successful Reversal of Diabetes in Nude Mice by Transplantation of Microencapsulation Porcine Neonatal Islet Cell Aggregation," *Transplant. Proc.* 27:3212.
Krejchi et al. (1994) "Chemical Sequence Control of β-Sheet Assembly in Macromolecular Crystals of Periodic Polypeptides," *Science* 265:1427-1432.
Krych et al. (1992) "Complement Receptors," *Curr. Opin. Immunol.* 4:8-13.
Kuan et al. (1994) "Pseudomonas Exotoxin A Mutants. Replacement o Surface Exposed Residues in Domain II with Cysteine Residues that can be Modified with Polyethylene Glycol in a Site-Specific Manner," *J. Biol. Chem.* 269:7610-7616.
Kuhlenschmidt et al. (1983) "Specificity of Chicken Liver Carbohydrate Binding Protein," *Biochem.* 23(16):3569-3575.
Kuhner et al. (1994) "Lipid Mono- and Bilayer Supported on Polymer Films: Composite Polymer-Lipid Films on Solid Substrates," *E. Biopys. J.* 67:217-226.
Kurfurst, M.M. (1992) "Detection and Molecular Weight Determination of Polyethylene Glyol-Modified Hirudin by Staining After Sodium Dodecyl Sulfate-Polyacrylamide Gel Electrophoresis," *Anal. Biochem.* 200:244-248.
Lamparski et al. (1993) "Thermotropic Properties of Model Membranes Composed of Polymerizable Pipids. 1. Phosphatidylcholines Containing Terminal Acryloyl, Methacryloyl, and Sorbyl Groups," *J. Am. Chem. Soc.* 115:8096-8102.
Lamparski et al. (1992) "Photoinduced Destabilization of Liposomes," *Biochem.* 31:685-694.
Laster et al. (1988) "Heparin-Coated Catheters and Heparin-Induced Thrombocytopenia," *J. Vasc. Surg.* 7(5);667-672.
Lee et al. (Aug. 2000) "Thermo-Reversible Self-Assembly of Nanoparticles Derived from Elastin-Mimetic Polypeptides," *Adv. Mater.* 12(15):1105-1110.
Lenschow et al. (1992) "Long-Term Survival of Xenogeneic Pancreatic Islet Grafts Induced cy CTLA4Ig," *Science* 257:789-795.
Lim et a. (1980) "Microencapsulated Islet as a Bioartificial Endocrine Pancreas," *Science* 210:908-910.
Lindhout et al. (1995) "Antithrombin Activity of Surface-Bound Heparin Studied Under Flow Conditions," *J. Biomed. Mater. Res.* 29(10):1255-1266.
Linder et al. (1990) "Basic Fibroblast Growth Factor Stimulates Endothelial Regrowth and Proliferation in Denuded Arteries," *J. Clin. Invest.* 85:2004-2008.
Loudovaris et al. (1992) "The Role of T Cells in the Destruction of Xenografts Within Cell Impermeable Membranes," *Transplant. Proc.* 24:2938.
Loykulnant et al. (2000) "Protection and Polymerization of Functional Monomers. 30. Anionic Living Polymerization of 4-Alkylstyrenes Containing Acetal-Protected Monosaccharide Residues," *Macmol.* 33:4757-4764.
Loykulnant et al. (1998) "Protection and Polymerization of Functional Monomers. 28. Anionic Livining Polmerization of Styrene Derivatives Containing Acetal-Protected Monosaccharide Residues," *Macromol.* 31:9121-9126.
Lu et al. (1996) "Comparison of Activated Protein C/Protein S-Mediated Inactivation of Human Factor VIII and Factor V," *Blood* 87(11):4708-4717.
Lvov et al. (1993) "Assembly, Structural Characterization, and Thermal Behavior of Layer-by-Layer Deposited Ultrathin Films of Poly(Vinyl Sulfate) and Poly(allylamine)," *Langmuir* 9:481-486.
MacDonald et al. (1991) "Small-Volume Extrusion Apparatus for Preparation of Large, Unilamellar Vesicles," *Biochim. Biophys. Acta.* 1061:297-303.
Manjula et al. (2003) "Site-Specific PEGylation of Hemoglobin at cys-93(Beta): Correlation Between the Colligative Properties of the PEGylated Protein and the Length of the Conjugates PEG Chain," *Bioconjug. Chem.* 14:464-472.
Mann et al. (1988) "Cofactor Proteins in the Assembly and Expression of Blood Clotting Enzyme Complexes," *Ann. Rev. Biochem.* 57:915-956.
Mao et al. (1995) "Interactions, Structure and Stability of Photoreactive Bolaform Amphiphile Multilayers," *Langmuir* 11:942-952.
Maoz et al. (1984) "On the Formation and Structure of Self-Assembling Monolayers," *J. Colloid Interface Sci.* 100(2):465-496.
Markovich et al. (1991) "Silica Subsurface Amine Effect on the Chemical Stability and Chromatographic Properties of End-Capped Immobilized Artificial Membrane Surfaces," *Anal. Chem.* 63:1851-1860.
Marra et al. (1997) "Cytomimetic Biomaterials. 1. In-Situ Polymerization of Phospholipids on Alklated Surface," *Macromol.* 30(21):6483-6488.
Marra et al. (1997) "Cytomimetic Biomaterials. 2. in-Situ Polymerization of Phospholipids on a Polymer Surface," *Langmuir* 13:5697-5701.
Marra et al. (1997) "Stabilized Phosphatidylcholine Surfaces Via In-Situ Polymerization at a Solid-Liquid Interface," *Polymer Preprints* 38(2):682-683.
Marsh et al. (1999) "Atom Transfer Polymerization: Use of Uridine and Adenosine Derivatized Monomers and Initiators," *J. Macromol.* 32:8725-8731.
Martin et al. (1997) "Processing and Characterization of Protein Polymers," In; *Protein-Based Materials*, McGrath et al. Eds., Birkhauser: Boston, pp. 339-370.
Martin et al. (1994) "General Method for the Synthesis of Phospholipid Derivatives of 1,2-*O*-diacyl-*sn*-Glycerols," *J. Org. Chem.* 59:4805-4820.
Massia et al. (1992) "Vascular Endothelial Cell Adhesion and Spreading Promoted by Peptide REDV of the IICS Region of Plasma Fibronectin is Mediated by Integrin $\alpha_2\beta_1$," *J. Biol. Chem.* 267:14019-14026.
Mathew et al. (1993) "Complex Coacervate Microcapsules for Mammalian Cell Culture and Artificial Organ Development," *Biotechnol. Prog.* 9:510-519.

Mauk et al. (1998) "Structural Characterization of Self-Assembled Lipid Monolayers by *NπT*Simulation," *Langmuir* 14:5255-5266.
Mauk et al. (1960), "Vesibio Targeting: Timed Release and Specificity for Leukocytes in Mice by Subcutaneous Injection," *Science* 207:309-311.
McLean et al. (1983) "Preparation of Stable Polar Surfaces Using Polymerizable Long-Chain Diacetylene Molecules," *Thin Solid Films* 99:127-131.
McMillan et al. (2000) "Synthesis and Characterization of Elastin Mimetic Protein Gels Derived from a Well-Defined Polypeptide Precursor," *Macromol.* 33:4809-4821.
McMillan et al. (1999) "High-Resolution Topographic Imaging of Environmentally Responsive, Elastin-Mimetic Hydrogels," *Macromol.* 32:9067-9070.
McMillan et al. (1999) "Rapid Assembly of Synthetic Genes Encoding Protein Polymers," *Macromol.* 32:3643-3648.
McPherson et al. (1996) "Product Purification by Reversible Phase Transition Following *Eschericia coli* Expression of Genes Encoding up to 251 Repeats of the Elastomeric Pentapeptide GVGVP," *Protein Exp. Purification* 7:51-57.
McPherson et al. (1992) "Production and Purification of a Recombinant Elastomeric Polypeptide, G-$(VPGVG)_{19}$-VPGV, from *Escherichia coli," Biotechnol. Prog.* 8:347-352.
Merrill et al. (1970) "Polyvinyl Alcohol-Heparin Hydrogel 'G'," *J. Appl. Physi.* 29(5):723-730.
Meuse et al. (1998) "Hybrid Bilayer Membranes in Air and Water: Infrared Spectroscopy and Neutron Reflectivity Studies," *Biophys. J.* 74:1388-1398.
Mielczarski et al. (1989) "Fourier Transform Infrared External Reflection Study of Molecular Orientation in Spontaneously Adsorbed Layers on Low-Absorption Substrated," *J. Phys. Chem.* 93:2034-2038.
Miller et al. (1988) "Both the Lyt-$2^+$and L3T4$^+$T Cell Subsets are Required for the Transfer of Diabetes in Nonobese Diabetic Mice," *J. Immunol.* 140:52-58.
Minoda et al. (1995) "Synthesis of Functional Polymers Bearing Pendant Mono- and Oligo- Saccharide Residues," *Macromol. Symp.* 99:169-177.
Miyata et al. (1997) "Polymers with Pendent Saccharides—'Glycopolymers'," *Trends Polymer Sci.* 5:198-206.
Miyoshi et al. (1976) "A Rapid Formation of Lysine-Derived Crosslinks by Chick Embryo Aorta," *J. Biochem.* (Tokyo) 79:1235-1243.
Monkarsh et al. (1997) "Positional Isomers of Monopegylated Interferon α-2a: Isolation, Characterization, and Biological Activity," *Anal. Biochem.* 247(2):434-440.
Monshipouri et al. (1995) "Liposome-Encapsulated Alginate: Controlled Hydrogel Particle Formation and Release," *Microencapsulation* 12(2):117-127.
Moore et al. (1983) "Ion-Binding Properties of Poly(iminomethylene(*cis*-tetrahydro-2,5-furandiyl)carbonyl) and Poly(oxymethylene(*cis*-tetrahydro-2,5-furandiyl)-carbonyl)," *Macromol.* 16:338-339.
Morpurgo et al. (1996) "Preparation and Characterization of Poly(Ethylne Glycol) Vinyl Sulfone," *Boconjug. Chem.* 7:363-368.
Moses et al. (1990) "Xenogeneic Proliferation and Lymphokine Production are Dependent Upon CD4+ Helper T Cells and Self Antigen-Presenting Cells in the Mouse," *Exp. Med.* 172:567-575.
Moya et al. (2000) "Lipid Coating on Polyelectrolyte Surface Modified Colloidal Particles and Polyeletrolyte Capsules," *Macromol.* 33:4538-4544.
Muller-Eberhard, H.I. (1988) "Molecular Organization and Function of the Compliment System," *Ann. Rev. Biochem.* 57:321-347.
Nagahori et al. (2001) "Tailored Glycolpolymers: Controlling the Carbohydrate-Protein Interaction Based on Template Effect," *Biomacromolecules* 2:22-24.
Nagashima et al. (1993) "Alanine-Scaning Mutagenesis of the Epidermal Growth Factor-Like Domains of Human Thrombomodulin Identifies Critical Residues for its Cofactor Activity," *J. Biol. Chem.* 268:2888-2892.
Nagle et al. (1996) "X-Ray Structure Determination of Fully Hydrated $L_α$ Phase Dipalmitoylphosphatidylcholine Bilayers," *Biophys. J.* 70:1419-1431.
Nah et al. (2000)"Polymeric Micelle Formation of Multiblock Copolymer Composed of Poly(γ-Benzyl *L*-Glutamate) and Poly(Ethylene Oxide)," *Bull. Korean Chem. Soc.* 21(4):383-388.
Nah et al. (2000) "Drug-Delivery System Based on Core-Shell-Type Nanoparticles Composed of Poly(γ-Benzyl *L*-Glutamate) and Poly(Ethylene Oxide)," *J. Appl. Polymer Sci.* 75:1115-1126.
Nemerson et al. (1991) "The Effect of Flow on Hemostasis and Thrombosis," *Thromb. Haemost.* 66(3):272-276.
Nickerson et al. (1993) "Analysis of Cytokine Transcripts in Mancreatic Islet Cell allografts During Rejection and Tolerance Induction," *Transplantation Proc.* 25:984-985.
Nielsen et al. (Apr. 1988) "Glycolamide Esters as Biolabile Prodrugs of Carboxylic Acid Agents: Synthesis, Stability, Bioconversion, and Physicochemical Properties," *J. Pharm. Sci.* 77(4):285-298.
Nojiri et al. (1996) "Can Heparin Immobilized Surfaces Maintain Immobilized Polymer Surfaces," *ASAIO J.* 42(5):M468-M475.
Nojiri et al. (1990) In Vivo Nonthrombogenicity of Heparin Immobilized Polymer Surfaces, *ASAIO Trans.* 36(3):M168-M172.
Nomura et al. (1996) "Preparation of 'Sugar-coated' Homopolymers and Multiblock ROMP Copolymers," *Macromol.* 29:540-545.
O'Brien et al. (1998) "Polymerization of Preformed Self-Organized Assemblies," *Acc. Chem. Res.* 31:861-868.
O'Connell et al. (1993) "Unmodified Pancreatic Islet Allograft Rejection Results in the Preferential Expression of Certain T Cell Activation Transcripts," *J. Immunol.* 150:1093-1104.
O'Donnell et al. (1992) "Radiation Degradation of Linear Low Density Polyethylene: Determination of Lamellae Thickness, Crystallinity and Crosslinking by Solid-State $^{13}$CNMR and DSC," *Rad. Phys. Chem.* 36(20):209-214.
O'Donnell et al. (1992) "A Solid-State $^{13}$C-NMR Study of Crosslinking in Polybutadiene by γ Radiation: Effect of Microstructure and Dose," *J. Polym. Chem. Ed.* 30:185-195.
Ohno et al, (1999) "Nitroxide-Controlled Free Radical Polymerization of a Sugar-Carrying Acryloyl Monomer," *Macromol. Chem. Phys.* 200:1619-1625.
Ohno et al. (1998) "Synthesis of a Well-Defined Glycopolymer by Nitroxide-Controlled Free Radical Polymerization," *Macromol.* 31:1064-1069.
Ohno et al. (1998) "Synthesis of a Well-Defined Glycopolymer by Atom Transfer Radical Polymerization," *J. Polym. Sci. A. Polym. Chem.* 36:2473-2481.
Ohno et al. (1998) "Free Radical Polymerization of a Sugar Residue-Carryinr Styryl Monomer with a Lipophilic Alkoxyamine Initiator: Synthesis of a Well-Defined Novel Glycolipid," *Macromol. Chem. Phys.* 199:2193-2197.
Ohno et al. (1987) "Polymerization of Liposomes Composed of Diene-Containing Lipids by UV and Radical Initiators: Evidence for the Different Chemical Environment of Diene Groups on 1- and 2-Acyl Chains," *Macromol.* 20:929-933.
Ohno et al. (1987) "Polymerization of Liposomes Composed of Diene-Containing Lipids by Radical Initiators. II. Polymerization of Monodiene-Type Lipids as Liposomes," *J. Polym. Sci. A. Polym, Chem.* 25.2737-2746.
Orban et al. (2000) "Cytomimetic Biomaterials, 4, In-Situ Photopolymerization of Phospholipids on an Alkylated Surface," *Macromol.* 33(11):4205-4212.
Ormitz et al. (1995) "FGF Binding and FGF Receptor Activation by Synthetic Heparan-Derived Di- and Trisaccharides," *Science* 268:432-434.
Otani et al. (1996) "Rapidly Curable Biological Glue Composed of Gelatin and Poly(L-Glutamic Acid)," *Biomater*, 17(14):1387-1391.
Owen et al. (1981) "Functional Properties of an Andothelial Cell Cofactor for Thrombin-Catalyzed Activation of Protein C," *J. Biol. Chem.* 256(11):5532-5535.
Packer et al. (1984) "The Effects of Morphology on $^1$H NMR Spectra and Relaxation in Semicrystalline Polyolefins," *J. Polym. Sci. Polym. Phys.* 22:569-616.
Panitch et al. (1999) "Design and Biosynthesis of Elastin-Like Artificial Extracellular Matrix Proteins Containing Periodically Spaced Fibronectin CS5 Domains," *Macromol.* 32:1701-1703.
Parikh et al. (1994) "An Intrinsic Relationship Between Molecular Structure in Self-Assembled *n*-alkysiloxane Monolayers and Deposition Temperature," *J. Phys. Chem.* 98:7577-7590.

Parker et al. (1996) "Transplantation of Discordant Xenografts: A Challenge Revisited," *Immunol. Today* 17:373-378.
Parkinson et al. (1992) "Structure-Function Studies of the Epidermal Growth-Factor Domains of Human Thrombomodulin," *Biochem. Biophys. Res. Commun*. 185:567-576.
Pasquali-Ronchetti et al. (1998) "Study of Elastic Fiber Organization by Scanning Force Microscopy," *Matrix Biol*. 17:75-83.
Pasquali-Ronchetti et al. (1995) "Ultrastructure of Elastin," *Ciba Foundation Symp*. 192:31-50.
Pearce et al. (1993) "Comparison of the Membrane Binding Kinetics of Bovine Prothrombin and Its Fragment 1," *J. Biol. Chem*. 268:22984-22991.
Peterson et al. (1996) "Transfer of Diabetes in the NOD-*scid* Mouse by CD4 T-Cell Clones: Differential Requirement for CD8 T-Cells," *Diabetes* 45:328-336.
Petka et al. (1998) "Reversible Hydrogels from Self-Assembling Artificial Proteins," *Science* 281:389-392.
Petitou et al. (1999) "Synthesis of Thrombin-Inhibiting Heparin Mimetics Without Side Effects," *Nature* 398:417-422.
Petitou et al. (1998) "First Synthetic Carbohydrates with the Full Anticoagulant Properties of Heparin," *Chem. Int. Ed*. 37:3009-3014.
Pierson et al. (1989) "$CD4^+$ Lymphocytes Plat a Dominant Role in Murine Xenogeneic Responses," *Trans. Proc*. 21:519.
Plant et al. (1995) "Phospholipid/Alkanethiol Bilayers for Cell-Surface Receptor Studies by Surface Plasmon Resonance," *Anal. Biochem*. 226:342-348.
Plant, A.L. (1993) "Self-Assembled Phospholipid/Alkanethiol Biomimetic Bilayers on Gold," *Langmuir* 9:2764-2767.
Plant et al. (1989) "Generic Liposome Reagent for Immunoassays," *Anal. Biochem*. 176:420-426.
Ponpipom et al. (1980) "Isolation of 1,3-Distearoyl-Glycero-2-Phosphocholine (β-Lectin) from Commercial 1,2-Distearoyl-*sn*-Glycero-3-Phosphocholine," *Lipid Res*. 21:136-139.
Pourdeyhimi et al. (1999) "Measuring Fiber Diameter Distribution in Nonwovens," *Textile Res. J*. 69:233-236.
Qiu et al. (1994) "Protein Kinase C-Dependent and -Independent Pathways of Mitogen-Activated Protein Kinase Activation in Macrophages by Stimuli that Activate Phospholipase $A_2$," *J. Biol. Chem*. 269:19480-19487.
Rand et al. (1996) "Blood Clotting in Minimally Altered Whole Blood," *Blood* 88(9):3432-3445.
Rapaka et al. (1978) "Non-Elastomeric Polypeptide Models of Elastin," *Int. J. Pept. Protein Res*. 11:109-127.
Regen et al. (1983) "Polymer-Supported Membranes. A New Approach for Modifying Polymer Surfaces," *Macromol*. 16:335-338.
Reneker et al. (1996) "Nanometre Diameter Fibers of Polymer, Produced by Electrospinning," *Nanotechnol*. 7:216-223.
Reneker et al. (1995) "Electrospun Polyaramid Fibers: Structure and Morphology," *Bull. Am. Phys. Soc*. 40:351 Abstract.
Rifkin et al. (1989) "Recent Developments in the Cell Biology of Basic Fibroblast Growth Factor," *J. Cell. Biol*. 109:1-6.
Ringsdorf et al. (1988) "Molecular Architecture and Function of Polymeric Oriented System: Models for the Study of Organization, Surface Recognition, and Dynamics of Biomembranes," *Angew Chem. Int. Ed. Engl*. 27:113-158.
Roach et al. (1957) "The Reason for the Shape of the Distensibility Curves of Arteries," *Can. J. Biochem. Physiol*. 25:681-690.
Roberts et al. (1996) "Dopamine Secretion by PC12 Cells Microencapsulated in a Hydroxymethyl Methacrylate-Methyl Methacrylate Copolymer," *Biomater*. 17:267-275.
Roberts et al. (2002) "Chemistry for Peptide and Protein PEGylation," *Adv. Drug Deliv. Rev*. 54:459-476.
Robins et al. (1982) "Analysis of the Crosslinking Components in Collagen and Elastin," *Methods Biochem. Anal*. 28:329-379.
Rosen et al. (1991) "Regulation of Motility in Bovine Brain Endothelial Cells," *J. Cell. Physiol*. 146:325-335.
Roy et al. (2000) "Synthesis and Fluorescence Properties of New Fluorescent, Polymerizable, Metal-Chelating Lipids," *J. Org. Chem*. 65:3644-3651.
Roy, R. (1997) "Recent Developments in the Rational Design of Multivalent Glycoconjugates," *Top. Curr. Chem*. 187:241-274.
Roy, R. (1996) "Synthesis and Some Applications of Chemically Defined Multivalent Glycoconjugates," *Curr. Opin. Struct. Biol*. 6:692-702.
Sabatani et al. (1987) "Organized Self-Assembling Monolayers on Electrodes. 2. Monolayer-Based Ultramicroelectrodes for the Study of Very Rapid Electrode Kinetics," *J. Phys. Chem*. 91:6663-6669.
Sackmann et al. (2000) "Supported Membranes on Soft Polymer Cushions: Fabrication, Characterization and Applications," *Trans. Biotechnol*. 18:58-64.
Sadler, J.E. (1997) "Thrombomodulin Structure and Function," *Thromb. Haemst*. 78:392-395.
Sakai et al. (1998) "Molecular Orientation in Langmuir Film of 12-Hydroxystearic Acid Studied by Infrared External-Reflection Spectroscopy," *Langmuir* 1:6249-6255.
Sakata et al. (1985) "Activated Protein C Stimulates the Fibrinolytic Activity of Cultured Endothelial Cells and Decreases Antiactivator Activity," *Proc. Nat. Acad. Sci. USA* 82(4):1121-1125.
Sandberg et al. (1985) "Elastin Covalent Structure as Determined by Solid Phase Amino Acid Sequencing," *Pathol. Biol*. 33:266-274.
Sandberg et al. (1981) "Elastin Structure, Biosynthesis, and Relation to Disease States," *N. Eng. J. Med*. 304:566-579.
Sandberg et al. (1977) "Primary Structure of Porcine Tropoelastin," *J. Adv. Exp. Med. Biol*. 79:277-284.
Santin et al. 1996 "Synthesis and Characterization of a New Interpenetrated Poly(2-Hydroxyethylmethacrylate)-Gelatin Composite Polymer," *Bioamterials* 17(15):1459-1467.
Sato et al. (1988) "Autocrine Activities of Basic Fibroblast Growth Factor: Regulation of Endothelial Cell Movement, Plasminoen Activator Synthesis and DNA Synthesis," *J. Cell. Biol*. 107:1199-1205.
Saxon et al. (2000) "Cell Surface Engineering by a Modified Staudinger Reaction," *Science* 287:2007-2010.
Schmidt et al. (1989) "Recent Developments in the Synthesis of Glycoconjugates," *Pure Appl. Chem*. 61(7):1257-1270.
Sefton, M.V. (1989) "Blood, Guts, and Chemical Engineering," *Can J. Chem. Eng*. 67:705-712.
Seifert et al. (1993) "Charge Transport by Ion Translocating Membrane Proteins on Solid Supported Membranes," *Biophs. J*. 64:384-391.
Seitz et al. (1998) "Formation of Tethered Supported Bilayers Via Membrane-Inserting Reactive Lipids," *Thin Solid Films* 329:767-771.
Sells et al. (1994) "Two-Dimensional Polymerization of Lipid Bilayers: Degree of Polymerization of Acryloyl Lipids," *Macromol*. 27:226-233.
Serruys et al. (1998) "Randomised Comparison of Implantation of Heparin-Coated Stents with Baloon Angioplasty in Selected Patients with Coronary Artery Disease (Benestent II)," *Lancet* 352:673-681.
Shen et al. (2001) "Polymer-Supported Lipid Bilayers on Benzophenone-Modified Substrates," *Biomacromol*. 2:70-79.
Shi et al. (2001) "Release Behavior of Thin-Walled Microcapsules Composed of Polyelectrolte Multilayers," *Langmuir* 17:2036-2042.
Shoji et al. (1993) "Human and Baboon Integrin $\beta_5$ Subunit-Encoding MRNAs Have Alternative Polyadenylation Sites," *Gene* 133:307-308.
Shultz et al. (1995) "Multiple Defects in Innate and Adaptive Immunologic Function in NOD/LtSz-*scid* Mice," *J. Immunol*. 154:180-191.
Siedlecki et al. (1994) "Interactions of Human Von Willebrand Factor with a Hydrophobic Self-Assembled Monolayer Studied by Atomic Force Microscopy," *Biomed. Mater. Res*. 28:971-980.
Slack et al. (1993) "The Effects of Flow on Blood Coagulation and Thrombosis," *Thromb. Haemost*. 70(1):129-134.
Slack et al. (1994) "Flow Chambers and Their Standardization for Use in Studies of Thrombosis," *Thromb. Haemost*. 72(5) :777-781.
Smirnov et al. (1999) "The Effect of Membrane Composition on the Hemostatic Balance," *Biochem*. 38(12):3591-3598.
Smirnov et al. (1994) "Phosphatidylethanolamine Incorporation into Vesicles Selectively Enhances Factor Va Inactivation by Activated Protein C," *J. Biol. Chem*. 269(2):816-819.
Snyder et al. (1978) "Vibrational Spectra in the C-H Stretching Region and the Structure of the Polymethylene Chain," *Spectrochim. Acta. A* 34A:395-406.

Solletti et al. (1996) "Elaboration and Characterization of Phospholipid Langmuir-Blodgett Films," *Langmuir* 1:5379-5386.
Spinke et al. (1992) "Polymer-Supported Bilayer on a Solid Substrate," *Biophys. J.* 63:1667-1671.
Stoll et al. (1988) "Improved Procedure for the Construction of Neoglycolipids Having Antigenic and Lactin-Binding Activities, from Reducing Oligosaccharides," *Biochem. J.* 256:661-664.
Sun et al. (1993) "Ultrathin Self-Assembled Polymeric Films on Solid Surfaces. 2. Formation of 11-(*n*-Pentyldithio)undecanoate-Bearing Polyacrylate Monolayers on Gold," *Langmuir* 9:3200-3207.
Sun et al. (1996) "Spontaneous Polymer Thin Film Assembly and Organization Using Mutually Immiscible Side Chains," *J. Am. Chem. Soc.* 118:1856-1866.
Sun et al. (1994) "Ultrathin Self-Assembled Polymeric Films on Solid Surfaces. III. Influence of Arcylate Dithioalhyl Side Chain Length on Polymeric Monolayer Formation on Gold," *J. Vac. Sci. Technol.* 12:2499-2506.
Sun et al. (1998) "The Synthesis of Neoglycophospholipid Conjugates Via Reductive Animation of ω-Oxoalkylycosides and Phosphatidylethanolamines," *Carb. Res.* 370:77-81.
Sun et al. (1997) "Neoglycophospholipids with Alkyl Spacers: Synthesis Via an Improved Reductive Animation and Monolayer Properties," *Bioconjug. Chem.* 8:567-571.
Sun et al. (1996) "Normalization of Diabetes in Spontaneously Diabetic Cynomologus Monkeys by Xenografts of Microencapsulated Porcine Islets Without Immunosuppression," *J. Clin. Invest.* 98:1417-1422.
Sun et al. (2006) "Carbohydrate and Protein Immobilization onto Solid Surfaces by Sequential Diels-Alder and Azide-Alkyne Cycloadditions," *Bioconjug. Chem.* 17:52-57.
Suzuki et al. (1988) "Thrombomodulin Precursor," NCBI Accession No. P07204.
Takeuchi et al. (1992) "Heart Allografts in Murine Systems: The Differential Activation of Th2-Like Effector Cells in Peripheral Tolerance," *Transplant.* 53:1281-1294.
Tasumi at al. (1962) "Normal Vibrations and Force Constants of Polymethylene Chain," *J. Mol. Spectrosc.* 9:261-287.
Tendian et al. (1991) "Evidence from Total Internal Reflection Fluorescence Microscopy for Calcium-Independent Binding of Prothromnbin to Negatively Charged Planar Phospholipid Membranes," *Biochem.* 30:10991-10999.
Terranova et al. (1985) "Human Endothelial Cells are Chemotactic to Endothelial Cell Growth Factor and Heparin," *Cell. Biol.* 101:2330-234.
Thomas et al. (1987) "Raman Amide Bands of Type-II β-Turns in Cyclo-$(VPGVG)_3$ and Poly(VPGVG), and Implications for Protein Secondary-Structure Analysis," *Biopolymers* 26:921-934.
Toshima et al. (1993) "Recent Progress on *O*-Glycosylation Methods and Its applications to Natural Products Synthesis," *Chem. Rev.* 93:1503-1531.
Tseng et al. (Apr. 2006) "Membrane-Mimetic Films Containing Thrombomodulin and Heparin Inhibit Tissue Factor-Induced Thrombin Generation in a flow Model," *Biomater.* 27(12):2637-2650.
Tseng et al. (May 2006) "Catalytic Efficiency of Thrombomodulin-Functionalized Membrane-Mimetic Film in a Flow Model," *Biomater.* 27(13):2768-2775.
Tsutsumi et al. (2000) "Site-Specific Chemical Modification with Polyethylene Glycol of Recombinant Immunotoxin Anti-Tac(Fv)-PE38 (LMB-2) Improves Antitumor Activity and Reduces Animal Toxicity and Immunogenicity," *Proc. Nat. Acad. Sci. USA* 97:8548-8553.
Turitto et al. (1998) "Mechanical Factors Affecting Hemostasis and Thrombosis," *Thromb. Res.* 92(6Sup.2):S25-S310.
Ueda et al. (1992) "Preparation of 2-Methacryloyloxyethyl Phosphorylcholine Copolymers with Alkyl Methacrylates and Their Blood Compatibility," *Polym. J.* 24(11):1259-1269.
Uldag et al. (1993) "Metabolic Activity and Proliferation of CHO Cells in Hydroxyethyl Metharytate-Methyl Methacrylate (HEMA_MMA) Microcapsules," *Cell Transplant.* 2:175-182.
Urry et al. (1997) "Protein-Based Materials with a Profound Range of Properties and Applications: The Elastin $\Delta_1$, Hydrophobic Paradigm," McGrath et al. Eds., Birkhauser: Boston, pp. 133-177.
Urry et al. (1995) "Molecular Biophysics of Elastin Structure, Function and Pathology," *Ciba Foundation Symp.* 192:4-30.
Urry, D.W. (1993) "Molecular Machines: How Motion and Other Functions of Living Organisms can Result from Reversible Chemical Changes," *Angew. Chem, Int, Ed. Engle.* 32:819-841.
Urry et al. (1989). "Two-Dimensional Proton NMR Studies on Poly(VPGVG) and Its Cyclic Conformational Correlate, Cyclo$(VPGVG)_3$," *Biopolymers* 26:819-833.
Urry, D.W. (1988) "Entropic Elastic Processes in Protein Mechanisms. I. Elastic Structure Due to an Inverse Temperature Transition and Elasticity Due to Internal Chain Dynamics," *J. Prot. Chem.* 7(1):1-34.
Urry et al. (1986) "Polypentapeptide of Elastin," *Int. J. Pept. Protein Res.* 28:649-660.
Urry et al. (1985) "Polypentapeptide of Elastin, Temperature Dependence of Ellipticity and Correlation with Elastomeric Force," *Biochem. Biophys. Res. Commun.* 130:50-57.
Urry et al. (1985) "Phase-Structure Transitions of the Elastin Polypentapeptide-Water System within the Framework of Composition-Temperature Studies," *Biopolymers* 24:2345-2356.
Urry et al. (1975) "Studies on the Conformation and Interactions of Elastin Secondary Structure of Synthetic Repeat Hexapeptides," *Biochim. Biophys. Acta.* 393:296-306.
Urry et al. (1974) "Studies on the Conformation and Interactions of Elastin. Proton Magnetic Resonance of the Repeating Pentapeptide," *Biochem.* 13:609-616.
van Ackern et al. (1998) "Ultrathin Membranes for Gas Separation and Pervaporation Prepared Upon Electrostatic Self-Assembly of Polyelectrolytes," *Thin Solid Films* 329:762-766.
van Boeckel (1993) "The Unique Antithrombin III Binding Domain of Heparin: A Lead to New Synthetic Antithrombotics," *Chem Int. Ed. Engle.* 32(12):1671-1690.
Van Den Bulcke et al. (2000) "Structural and Rheological Properties of Methacrylamide Modified Gelatin Hydrogels," *Biomacromolecules* 1:31-38.
Vanderhart, D.L. (1990) "Proton Spin Diffusion as a Tool for Characterizing Polymer Blends," *Makromol. Chem. Macromol. Symp.* 34:125-159.
van't Veer (1997) "Inhibitory Mechanism of the Protein C Pathway on Tissue Factor-Induced Thrombin Generation," *J. Biol. Chem.* 272(12):7983-7984.
Vasilets et al. (1997) "Microwave $C0_2$ Plasma-Initiated Vapour Phase Graft Polymerization of Acrylic Acid onto Polytetrafluoroethylene for Immobilization of Human Thrombomodulin," *Biomater.* 18(17):139-1145.
Veronese, F.M. (2001) "Peptide and Protein PEGylation: A Review of Problems and is Solutions," Biomat. 22:405-417.
Viitala et al. (2000) "Protein Immobilization to a Partially Cross-Linked Organic Monolayer," *Langmuir* 16:4953-4961.
Wall et al. (1978) "Human Endothelial Cell Migration: Stimulation by a Released Platelet Factor," *Lab Invest.* 39(5):523-529.
Wang et al. (1993) "Synthesis of Phospholipid-Inhibitor Conjugates by Enzymatic Transphosphatidylation With Phospholipase D," *J. Am. Chem. Soc.* 115:10487-10491.
Wang et al. (2003) "Bioconjugation by Copper(I)-Catalyzed Azide-Alkyne [3+2] Cycloaddition," *J. Am. Chem. Soc.* 125(11):3192-3193.
Wasserman et al. (1990) "A Molecular Dynamics Investigation of the Elastomeric Restoring Force in Elastin," *Biopolymers* 29:1613-1631.
Wasserman et al. (1989) "The Structure of Self-Assembled Monolayers of Alkylsiloxanes on Silicon: A Comparison of Results from Ellipdometry and Low-Angle X-ray Reflectivity,".
Weber et al. (1997) "CTLA4-Ig Prolongs Survival of Microencapsulated Neonatal Porcine Islet Xenografts in Diabetic NOD Mice," *Cell Transplant.* 6(5):505-508.
Weber et al. (1995) "Encapsulated Islet Iso-, Allo, and Xenografts in Diabetic NOD Mice," *4 Trans. Proc.* 27:3308-3311.
Weber et al. (1994) "NOD Mouse Peritoneal Cellular Response to Poly-L-Lysine-Alginate Microencapsulated Rat Islets," *Trans. Proc.* 26:1116-1119.
Weber et al. (1990) "Microencapsulated Dog and Rat Islet Xenografts into Streptozotocin-Diabetic and NOD Mice," *Horm. Metab. Res.* 35:219-226.

Weber et al. (1990) "The Role id CD4$^+$ Helper T Cells in Destruction of Microencapsulation Islet Xenografts in NOD Mice," *Transplantation* 49(2):396-404.

Weber et al. (1999) "Long-Term Survival of Poly-L-Lysine-Alginate Microencapsulated Rat, Rabbit, and Pig Islet Xenografts in Spontaneously Diabetic NOD Mice," In, *Cell Encapsulation Technology and* Therapeutics, Kuhtreiber et al. eds., Ch. 11, Springer-Verlag, New York, pp. 117-137.

Weiler et al. (2003) "Thrombomodulin," *J. Thromb. Haemost.* 1:1515-1524.

Weiner et al. (1985) "Liposome-Collagen Gel Matrix: A Novel Sustained Drug Delivery System," *J. Pharm. Sci.* 74(9):922-925.

Welsh et al. (2000) "Engineering the Extracellular Matrix: A Novel Approach to Polymeric Biomaterials. I. Control of the Physical Properties of Artificial Protein Matrices Designed to Support Adhesion of Vascular Endothelial Cells," *Biomacromolecules* 1:23-30.

Westerduin et al. (1996) "Synthesis of Tailor-Made Glycoconjugates Showing AT III-Mediated Inhibition of Blood Coagulation Factors Xa and Thrombin," *Chem. Int. Ed. Engle.* 35:331-333.

Westman et al. (1995) "Synthesis and Fibroblast Growth Factor Binding of Oligosaccharides Related to Heparin and Heparan Sulphate," *J. Carb. Chem.* 14:95-113.

Wick et al. (1987) "Unusually Large Von Willebrand Factor Multimers Increase Adhesion of Sickle Erythrocytes to Human Endothelial Cells Under Controlled Flow." *J. Clin. Invest.* 80:905-910.

Widder et al. (1985) "Theory and Practice of Prodrug Kinetics," *Methods Enzymol.* 42:309-323.

Wilbur et al. (2000) "Biotin Reagents for Antibody Pretargeting. 4. Selection of Biotin Conjugates for In Vivo Application Based on their Dissociation Rate from Avidin and Streptavidin," *Bioconjug. Chem.* 11:569-583.

Winger et al. (1999) "Formation and Stability of Complex Membrane-Mimetic Monolayers on Solid Supports," *Langmuir* 15:3866-3874.

Winger et al. (1998) "Synthesis and Characterization of Supported Phospholipid Monolayers: A Correlative Investigation by Radiochemical Titration and Atomic Force Microscopy," *Langmuir* 14:4148-4155.

Winger et al. (1998) "Synthesis and Characterization of Supported Bioactive Lipid Membranes," In; *Materials Science of the Cell*, Plant et al. Eds., MRS Publications, Pittsburgh, pp. 113-118.

Winger et al. (1997) "Behavior of Lipid-Modified Peptides in Membrane-Mimetic Monolayers at the Air/Water Interface," *Langmuir* 13:3256-3259.

Winger et al. (1996) "Lipopeptide Conjugates: Biomolecular Building Blocks for Receptor Activating Membrane-Mimetic Structures," *Biomater.* 17:443-449.

Winger et al. (1995) "A Convenient Route to Thiol Terminated Peptides for Conjugation and Surface Functionalization Strategies," *Bioconjug. Chem.* 6:323-326.

Winger et al. (1995) "Purification of Synthetic Lipopeptide Conjugates by Liquid Chromatography," *J. Liquid Chromatogr.* 18:4117-4125.

Wohrle et al. (2001) "Comparison of the Heparin Coated vs the Uncoated Jostent—No Influence on Restenosis or Clinical Outcome," *Eur. Heart J.* 22:1808-1816.

Woghiren et al. (1993) "Protected Thiol-Polyethylne Glycol: A New Activated Polymer for Reversible Protein Modification," *Bioconjug. Chem.* 4:314-318b.

Wong et al. (1988) "Intriguing Absorption Band Behavior of IR Reflectance Spectra of Silicon Dioxide on Silicon," *Appl. Spectrosc.* 42(4):598-604.

Wood et al. (2003) "NMR Structures Reveal How Oxidation Inactivates Thrombomodulin," *Biochem.* 42:11932-11942.

Wright et al. (Oct. 2002) "Self-Assembly of Block Copolymers Derived from Elastin-Mimetic Polypeptide Sequences," *Adv. Drug Deliv. Rev.* 54(8):1057-1073.

Wright et al. (Feb. 2002) "Thermoplastic Elastomer Hydrogels Via Self-Assembly of an Elastin0Mimetic Triblock Polypeptide," *Adv. Funct. Mater.* 12:149-154.

Xiao et al. (1995) "Preparation, Structure, and Mechanical Stability of Alkylsilane Monolayers on Mica," *Langmuir* 11(5):1600-1604.

Yamada et al. (1999) "Controlled Synthesis of Amphiphilic Block Copolymers with Pendant *N*-acetyl-D-Glucosamine Residues by Living Cationic Polymerization and Their Interaction With WGA Lectin," *Macromol.* 32:3553-3558.

Yamada et al. (1997) "Controlled Synthesis of Glycopolymers with Pendant D-Glucosamine Residues by Living Cationic Polymerization," *J. Polym. Sci. A Polym. Chem.* 35:751-757.

Yamamoto et al. (2003) "Site-Specific PEGylation of a Lysine-Deficient TNF-Alpha with Full Bioactivity," *Nature Biotechnol.* 21:546-552.

Yen et al. (1989) "Infrared Reflectance Properties of Surface Thin Films," *J. Phys. Chem.* 93:7208-7216.

Yoshioka et al. (1990) "Encapsulation of Mammalian Cell With Chitosan-CMC Capsule," *Biotechnol. Bioeng.* 35:66-72.

Yu et al. (1997) "Smectic Ordering in Solutions and Films of a Rod-Like Polymer Owing to Monodispersity of Chain Length," *Nature* 389:167-170.

Zhang et al. (1989) "Synthesis of 4% Glu-Containing $Val^1$ and $Ile^1$-Polypentapeptides: Model Protein Systems for Demonstrating Mechanochemical Coupling," *J. Protein Chem.* 8:173-182.

Zierler et al. (1992) "Accuracy of Duplex Scanning for Measurement or Arterial Volume Flow," *J. Vasc. Sur.* 16(4):520-526.

US 5,556,632, 09/1996, Kohler et al. (withdrawn)

* cited by examiner

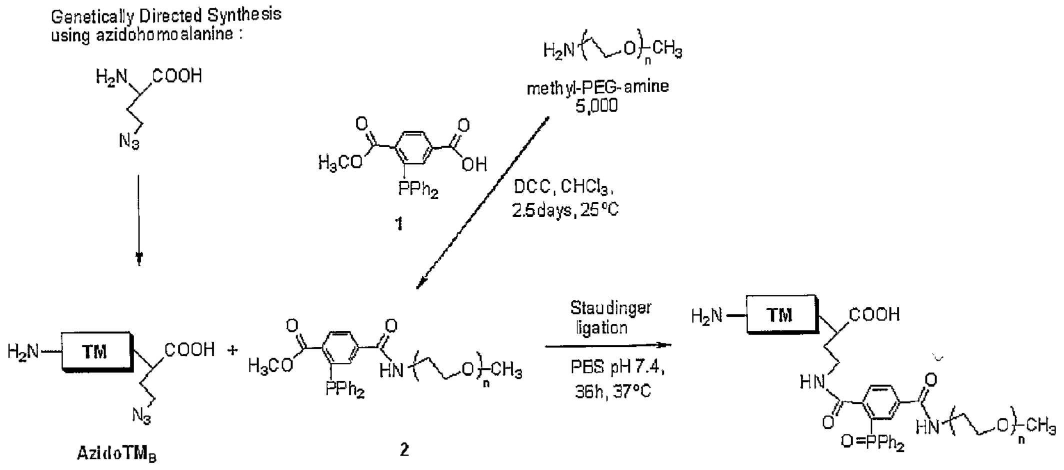
Scheme A
FIG. 1
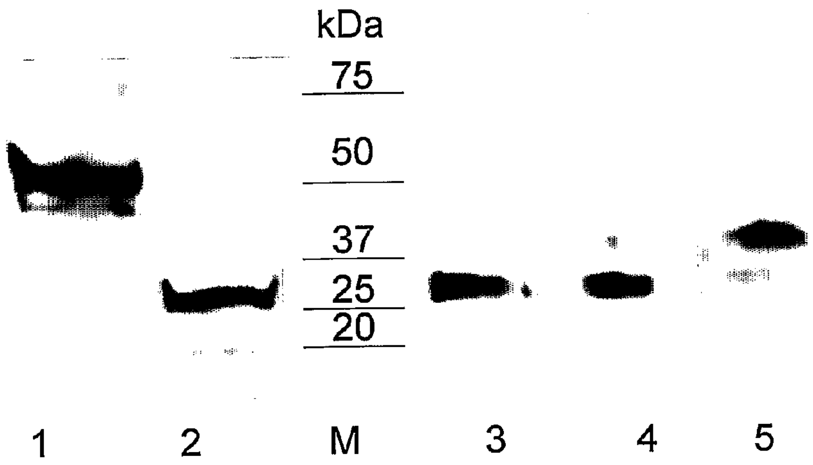
FIG. 2

Genetically Directed Synthesis using non-natural amino-acid :

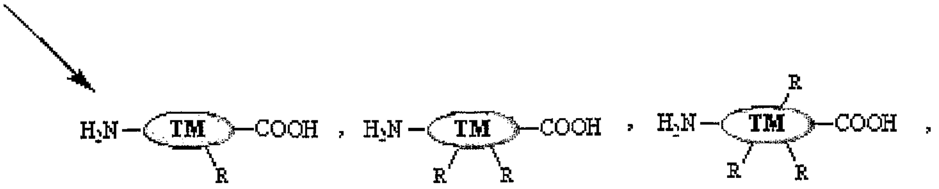

TM analogs containing NNAA

TM: Thrombomodulin analog capable of activating protein C
$NH_2$ : Amino group at the N-terminal of TM
COOH: Carboxylic acid group C-terminal of TM
NNAA: Non-Natural Amino Acid
R: Functional group of the non-natural amino acid ( $N_3$, alkyl, diene, ....)

Example of a Conjugation Reaction:

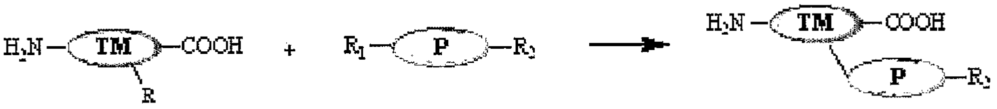

TM analog containing one NNAA | Linear polymer | TM conjugate

P: Linear or branched natural or synthetic polymer such as PEG, oligosaccharides, ...

$R_1$ : Alkyne, diene, 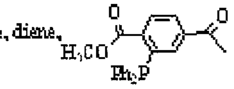 , ....

$R_2$ : - Functional group for anchoring onto surface : alkyne, diene, biotin, ....

- Anti-inflammatory/anti-thrombotic groups such as heparin, sialic acid Lewis X, ....

FIG. 5

SEQUENCE LISTING

```
<160> NUMBER OF SEQ ID NOS: 6

<210> SEQ ID NO 1
<211> LENGTH: 459
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (8)..(451)

<400> SEQUENCE: 1

ggatccc gac ccg tgc ttc aga gcc aac tgc gag tac cag tgc cag ccc       49
        Asp Pro Cys Phe Arg Ala Asn Cys Glu Tyr Gln Cys Gln Pro
        1               5                   10

ctg aac caa act agc tac ctc tgc gtc tgc gcc gag ggc ttc gcg ccc       97
Leu Asn Gln Thr Ser Tyr Leu Cys Val Cys Ala Glu Gly Phe Ala Pro
15                  20                  25                  30

att ccc cac gag ccg cac agg tgc cag ctg ttt tgc aac cag act gcc      145
Ile Pro His Glu Pro His Arg Cys Gln Leu Phe Cys Asn Gln Thr Ala
                35                  40                  45

tgt cca gcc gac tgc gac ccc aac acc cag gct agc tgt gag tgc cct      193
Cys Pro Ala Asp Cys Asp Pro Asn Thr Gln Ala Ser Cys Glu Cys Pro
            50                  55                  60

gaa ggc tac atc ctg gac gac ggt ttc atc tgc acg gac atc gac gag      241
Glu Gly Tyr Ile Leu Asp Asp Gly Phe Ile Cys Thr Asp Ile Asp Glu
        65                  70                  75

tgc gaa aac ggc ggc ttc tgc tcc ggg gtg tgc cac aac ctc ccc ggt      289
```

-continued

```
Cys Glu Asn Gly Gly Phe Cys Ser Gly Val Cys His Asn Leu Pro Gly
    80                  85                  90

acc ttc gag tgc atc tgc ggg ccc gac tcg gcc ctt gcc cgc cac att      337
Thr Phe Glu Cys Ile Cys Gly Pro Asp Ser Ala Leu Ala Arg His Ile
95                  100                 105                 110

ggc acc gac tgt gac tcc ggc aag gtg gac ggt ggc gac agc ggc tct      385
Gly Thr Asp Cys Asp Ser Gly Lys Val Asp Gly Gly Asp Ser Gly Ser
                115                 120                 125

ggc gag ccc ccg ccc agc ccg acg ccc ggc tcc acc ttg act cct ccg      433
Gly Glu Pro Pro Pro Ser Pro Thr Pro Gly Ser Thr Leu Thr Pro Pro
            130                 135                 140

gcc gtg ggg ggt atg taa tcggatcc                                     459
Ala Val Gly Gly Met
        145


<210> SEQ ID NO 2
<211> LENGTH: 147
<212> TYPE: PRT
<213> ORGANISM: Artificial
<220> FEATURE:
<223> OTHER INFORMATION: Synthetic Construct

<400> SEQUENCE: 2

Asp Pro Cys Phe Arg Ala Asn Cys Glu Tyr Gln Cys Gln Pro Leu Asn
1               5                   10                  15

Gln Thr Ser Tyr Leu Cys Val Cys Ala Glu Gly Phe Ala Pro Ile Pro
            20                  25                  30

His Glu Pro His Arg Cys Gln Leu Phe Cys Asn Gln Thr Ala Cys Pro
        35                  40                  45

Ala Asp Cys Asp Pro Asn Thr Gln Ala Ser Cys Glu Cys Pro Glu Gly
    50                  55                  60

Tyr Ile Leu Asp Asp Gly Phe Ile Cys Thr Asp Ile Asp Glu Cys Glu
65                  70                  75                  80

Asn Gly Gly Phe Cys Ser Gly Val Cys His Asn Leu Pro Gly Thr Phe
                85                  90                  95

Glu Cys Ile Cys Gly Pro Asp Ser Ala Leu Ala Arg His Ile Gly Thr
            100                 105                 110

Asp Cys Asp Ser Gly Lys Val Asp Gly Gly Asp Ser Gly Ser Gly Glu
        115                 120                 125

Pro Pro Pro Ser Pro Thr Pro Gly Ser Thr Leu Thr Pro Pro Ala Val
    130                 135                 140

Gly Gly Met
145


<210> SEQ ID NO 3
<211> LENGTH: 147
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (40)..(40)
<223> OTHER INFORMATION: Met-388-Leu substitution; position 40

<400> SEQUENCE: 3

Asp Pro Cys Phe Arg Ala Asn Cys Glu Tyr Gln Cys Gln Pro Leu Asn
1               5                   10                  15

Gln Thr Ser Tyr Leu Cys Val Cys Ala Glu Gly Phe Ala Pro Ile Pro
            20                  25                  30
```

-continued

```
His Glu Pro His Arg Cys Gln Leu Phe Cys Asn Gln Thr Ala Cys Pro
        35                  40                  45

Ala Asp Cys Asp Pro Asn Thr Gln Ala Ser Cys Glu Cys Pro Glu Gly
    50                  55                  60

Tyr Ile Leu Asp Asp Gly Phe Ile Cys Thr Asp Ile Asp Glu Cys Glu
65                  70                  75                  80

Asn Gly Gly Phe Cys Ser Gly Val Cys His Asn Leu Pro Gly Thr Phe
                85                  90                  95

Glu Cys Ile Cys Gly Pro Asp Ser Ala Leu Ala Arg His Ile Gly Thr
            100                 105                 110

Asp Cys Asp Ser Gly Lys Val Asp Gly Gly Asp Ser Gly Ser Gly Glu
        115                 120                 125

Pro Pro Pro Ser Pro Thr Pro Gly Ser Thr Leu Thr Pro Pro Ala Val
    130                 135                 140

Gly Gly Met
145


<210> SEQ ID NO 4
<211> LENGTH: 575
<212> TYPE: PRT
<213> ORGANISM: Homo sapiens

<400> SEQUENCE: 4

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255
```

-continued

```
Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
    370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
        435                 440                 445

Gly Phe Cys Ser Gly Val Cys His Asn Leu Pro Gly Thr Phe Glu Cys
    450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Pro Ala Val Gly Leu
            500                 505                 510

Val His Ser Gly Leu Leu Ile Gly Ile Ser Ile Ala Ser Leu Cys Leu
        515                 520                 525

Val Val Ala Leu Leu Ala Leu Leu Cys His Leu Arg Lys Lys Gln Gly
    530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
                565                 570                 575
```

<210> SEQ ID NO 5
<211> LENGTH: 21
<212> TYPE: DNA
<213> ORGANISM: Artificial
<220> FEATURE:
<223> OTHER INFORMATION: Synthetic construct

<400> SEQUENCE: 5
taccctaact acgacctggt g 21

<210> SEQ ID NO 6
<211> LENGTH: 18
<212> TYPE: DNA
<213> ORGANISM: Artificial
<220> FEATURE:

-continued

<223> OTHER INFORMATION: Synthetic construct

<400> SEQUENCE: 6
tatgagcaag cccgaatg 18

THROMBOMODULIN DERIVATIVES AND CONJUGATES

CROSS-REFERENCES TO RELATED APPLICATIONS

This application is the National Stage of PCT International Application No. PCT/US2005/005554, filed Feb. 22, 2005, which claims the benefit of U.S. Provisional Application No. 60/546,436, filed Feb. 20, 2004, both of which is are incorporated herein by reference in entirety to the extent not inconsistent with the disclosure herewith.

STATEMENT ON FEDERALLY SPONSORED RESEARCH OR DEVELOPMENT

This invention was made, at least in part, with government support under Grant No. NIH RO1HL56819 awarded by the National Institutes of Health. The government has certain rights in the invention.

BACKGROUND OF THE INVENTION

The transmembrane human protein thrombomodulin (TM), as a critical regulator of the protein C pathway, represents the major anticoagulant mechanism that is operative in both normal and injured blood vessels under physiologic conditions in vivo. An effective blood-contacting surface is dependent upon the presence of physiologically relevant antithrombogenic mechanisms that are incorporated into an engineered blood-material interface. Full length native human TM can be incorporated into membrane-mimetic films or surfaces by fusion/adsorption processes; a major drawback of these materials, however, is a loss of TM stability and/or functional activity with time. Moreover, in existing protocols for covalent immobilization of TM onto polymeric surfaces, the protein immobilization procedure involves freely available amino or carboxyl functionalities of TM, some of which may be within or near a bioactive site. The use of such functionalities can significantly reduce the functional bioactivity of TM after surface coupling. There is therefore a need for compositions and methods in this field to serve as effective alternatives.

SUMMARY OF THE INVENTION

In general the terms and phrases used herein have their art-recognized meaning, which can be found by reference to standard texts, journal references and contexts known to those skilled in the art. The following definitions are provided to clarify their specific use in the context of the invention.

When used herein, "thrombomodulin" refers to a protein molecule that is capable of involvement in the conversion of protein C to the activated protein C (protein Ca). In a particular example, the molecule relates to a specific endothelial cell receptor that forms a 1:1 stoichiometric complex with thrombin. In a preferred embodiment, the molecule is human and is also known as fetomodulin and CD141 antigen. In a particular embodiment, the term refers to a native molecule with nucleic acid or protein sequence information corresponding to that of accession number NM_000361, Version: NM_000361.2 GI:40288292; or Swiss-Prot: P07204.

When used herein, "derivative" refers to a variation or analog, or modification thereof, relative to a reference material. For example, a thrombomodulin derivative can refer to a mutant protein, truncation of a native protein sequence, or synthetically modified variant including modification by pegylation or conjugation such as to a polymer or surface. A derivative may employ the use of natural amino acids, non-natural amino acids, and/or other chemical moieties; whether covalently or non-covalently associated; and whether associated during translation, post-translation, or apart from translation such as in a synthetic approach; as disclosed herein or as would be understood in the art. In a particular embodiment, a derivative is a truncated, mutated, pegylated, conjugated thrombomodulin.

The following abbreviations are applicable. TM, thrombomodulin; PEG, polyethylene glycol.

It is recognized that regardless of the ultimate correctness of any mechanistic explanation or hypothesis, an embodiment of the invention can nonetheless be operative and useful.

In an embodiment, the present invention relates to the generation of novel thrombomodulin ("TM") conjugates, including soluble conjugates.

In an embodiment, the invention provides a method of site-specific PEGylation for a protein molecule. In a preferred embodiment, the protein molecule is bioactive thrombomodulin or a derivative thereof.

In an embodiment, a TM analog sequence comprises a catalytically active site capable of activating protein C (EGF 4-6 domains) and single or multiple non-natural amino acids. In a particular embodiment, TM analogs are conjugated to linear or branched natural or synthetic polymers via the non-natural amino acids. In an embodiment, the invention provides methods for conjugation of the TM conjugates to the surfaces of synthetic or natural materials, to targeting groups for site specific delivery of the agent, and/or to compounds that contain one or more additional anti-inflammatory/anti-thrombotic properties.

In an embodiment, a TM conjugate can be useful as a systemic agent for treatment of one or more conditions such as micro or macrovascular blood clots, stroke, heart attack, disseminated intravascular coagulation or other inflammatory or prothrombotic condition.

In an embodiment, the invention provides a coating of a surface of a medically implanted or human tissue or fluid contacting device. For example, implants or devices can include but are not restricted to: vascular grafts, stents, heart valves, dialysis membranes, membrane oxygenators, catheters, and guide wires to alter surface properties. A further embodiment of the invention provides a coating for living cells or tissues, including, but not restricted to smooth muscle cells, fibroblasts, endothelial cells, stem cells, chondrocytes, osteoblasts, pancreatic islets, or genetically engineered cells to establish or enhance the anti-inflammatory properties of the cells.

In an embodiment, the invention provides a covalent conjugation of truncated TM derivatives onto a blood or tissue contacting surface using natural or synthetic polymers as a spacer.

In an embodiment, the invention provides a novel method for covalent conjugation of TM to synthetic or natural materials site-specifically without loss of protein bioactivity or with substantial retention thereof. In a particular embodiment, the invention provides a relatively short recombinant TM construct containing EGF-like domains 4-6 and single or multiple non-natural amino acids optionally or preferably at the C-terminal portion of the construct. In a particular embodiment, the invention provides a modified TM through reaction with a suitable polymer spacer via one or more non-natural amino acids. In a particular embodiment, a TM is modified for further immobilization onto surfaces or for conjugation to linear or multifunctional natural or synthetic compounds that contain other anti-inflammatory or anti-thrombotic properties. In an embodiment, a bioconjugation reaction occurs in mild conditions to preserve TM bioactivity. In a preferred embodiment, polyethylene glycol ("PEG") is used as the polymer spacer.

In an embodiment, a modified construct is adapted for further immobilization onto a surface or for conjugation to linear or multifunctional natural or synthetic compounds that are capable of an anti-inflammatory or anti-thrombotic activity.

In an embodiment, PEGylation of a protein can confer one or more advantages, e.g. an increase in plasma half-life, stability against proteolytic cleavage, and a decrease of protein immunogenicity.

In an embodiment, the invention provides compositions including nucleic acid and protein molecules. In a particular embodiment, the compositions relate to sequences of the Table S1 below.

Table S1 of selected sequence listing information.

| SEQ ID NO: | Brief Description | Type |
|---|---|---|
| 1 | TMb | DNA/RNA |
| 2 | automatic translation | PRT |
| 3 | TMb | PRT |
| 4 | human TM | PRT |
| 5 | PCR primer | DNA |
| 6 | PCR primer | DNA |

In an embodiment, the invention provides methods and compositions relating to generation of thrombomodulin constructs comprising a non-natural amino acid. In an embodiment, a construct is thrombomodulin or a thrombomodulin derivative. In an embodiment, the invention provides recombinant expression or synthetic production of such constructs. In a preferred embodiment, the construct is generated by recombinant expression. In a preferred embodiment, the invention provides methods and compositions comprising an extracellular portion of thrombomodulin. In a preferred embodiment, the extracellular portion of thrombomodulin further comprises catalytically active sites. In a preferred embodiment, the extracellular portion of thrombomodulin is capable of activating protein C.

In a preferred embodiment, a thrombomodulin derivative comprises a single non-natural amino acid or multiple non-natural amino acids. In an embodiment, a non-natural amino acid can include those as would be understood in the art. For example, non-natural amino acids can include: methionine analogues, alanine analogues, phenylalanine analogues, leucine analogues, proline analogues and isoleucine analogues. An example of methionine analogues includes: L-2-amino-4-azido-butanoic acid.

In a preferred embodiment, a thrombomodulin derivative comprises a single non-natural amino acid at the C-terminal portion of the construct.

In an embodiment, the invention provides a thrombomodulin construct wherein the construct is conjugated to a natural or synthetic polymer or other natural molecule such as an antibody or other ligand recognition molecule. In an embodiment, the conjugation is via at least one non-natural amino acid in the recombinant protein.

In an embodiment, a synthetic polymer for conjugation to a construct can include a linear or branched synthetic polymer. For example, a linear or branched synthetic polymer can include: poly(t-butyl acrylate), poly(t-butyl methacrylate), polyacrylamide, glycolipid and their mimetics; and other polymers as would be understood in the art. Examples of a natural polymer include: glycoproteins and their mimetics, poly(arginine), polysaccharides and their mimetics; and other polymers as would be understood in the art. In an embodiment, a ligand recognition molecule is antifibrin antibody.

In an embodiment, a construct is conjugated to a linear or branched poly(ethylene glycol) molecule. In a preferred embodiment, the construct is conjugated to linear poly(ethylene glycol).

In an embodiment, the invention provides a thrombomodulin construct conjugated to a natural or synthetic polymer for surface anchoring. In an embodiment, the natural or synthetic polymer is multifunctional. In a preferred embodiment, the construct is conjugated to poly(ethylene glycol) for surface anchoring of the conjugate. In an example, an anchoring group includes: biotin, conjugated diene, azide, alkyne, diphenylphosphine, triarylphosphine; and other groups as would be understood in the art. In an example, a surface targeting group includes: sialyl-Lewis X; an antibody, Fab fragment or the like, or other analogous protein or non-protein recognition molecule (including an aptamer) capable of recognizing VCAM-1, ICAM-1, or other inflammatory cell surface proteins; antifibrin antibody; streptavidin, azide, alkyne, N-(ε-maleimidocaproyl; and others as would be understood in the art.

In an embodiment, a construct is conjugated to a synthetic polymer for anchoring to a surface of a synthetic material or a natural material. In an example, synthetic materials include: poly(tetrafluoroethylene), polysiloxanes, poly(ether urethane urea), poly(lactic acid-co-glycolic acid), a glass surface and derivatives; and other materials as would be understood in the art. In an example, natural materials include: cells, tissues, and blood vessels.

In an embodiment, the invention provides compositions and methods of a surface coating for a medically implanted or human tissue or fluid contacting device including but not restricted to vascular grafts, stents, heart valves, dialysis membranes, membrane oxygenators, catheters, or guide wires. In an embodiment, the surface coating alters a surface property of the implant or the device.

In an embodiment, the invention provides compositions and methods for coating a surface of living cells or tissues, including, but not restricted to smooth muscle cells, fibroblasts, endothelial cells, stem cells, chondrocytes, osteoblasts, pancreatic islets, or genetically engineered cells.

In an embodiment, the invention provides a recombinant thrombomodulin construct conjugated to a multifunctional natural or synthetic polymer, wherein the polymer is capable of an anti-inflammatory or anti-thrombotic property. In an embodiment, the construct is conjugated to a synthetic polymer comprising one or more anti-inflammatory groups. In an embodiment, the synthetic polymer comprises one or more additional anti-inflammatory groups. In an example, an anti-inflammatory group includes sialic acids and their mimetics/derivatives; and other groups as would be understood in the art.

In an embodiment, the invention provides a construct conjugated to a synthetic polymer further comprising an anti-coagulant or anti-thrombotic group. In an example, an anti-coagulant or anti-thrombotic group includes heparin and its mimetics/derivatives; and other groups as would be understood in the art.

In an embodiment, the invention provides a systemic agent for treatment of a medical condition, wherein the condition relates to a microvascular or macrovascular blood clot, stroke, heart attack, disseminated intravascular coagulation, or other inflammatory or prothrombotic condition. In an embodiment, the invention provides a method of treatment of the medical condition by administering to a patient in need a construct of the invention.

In an embodiment, the invention provides a truncated thrombomodulin protein derivative comprising EGF (4-6) like domains, a substitution of Leucine for methionine at position 388, and a GGM amino acid motif appended at a carboxy terminus of said derivative. In an embodiment, the GGM protein motif is expressed as a protein motif with a non-natural amino acid corresponding to the M amino acid residue. In an embodiment, the invention provides SEQ ID NO:3.

In an embodiment, the invention provides a truncated thrombomodulin derivative conjugate comprising a truncated thrombomodulin derivative and a polymer; wherein the thrombomodulin derivative comprises EGF (4-6) like domains, a substitution of Leucine for methionine at position 388, and a GGM amino acid motif appended at a carboxy terminus of said derivative. In an embodiment, the polymer comprises polyethylene glycol.

In an embodiment, the invention provides a truncated thrombomodulin nucleic acid derivative comprising EGF (4-6) like domains, a substitution of Leucine for methionine at position 388, and a nucleic acid sequence capable of encoding a Gly Gly Met motif appended at a carboxy terminus of said derivative. In an embodiment, the nucleic acid sequence comprises SEQ ID NO:1.

In an embodiment, the invention provides a method of generating a purified truncated thrombomodulin derivative protein, wherein the protein comprises EGF (4-6) like domains, a substitution of Leucine for methionine at position 388, and a non-natural amino acid; comprising the steps of providing a truncated thrombomodulin nucleic acid sequence; recombinantly expressing said nucleic acid sequence in the presence of a non-natural amino acid precursor; and purifying a recombinant expression product; thereby generating a purified truncated thrombomodulin derivative protein. In an embodiment, the nucleic acid sequence is SEQ ID NO:1.

BRIEF DESCRIPTION OF THE FIGURES

Scheme A. Synthesis of the methyl-PEG-triarylphosphine conjugate 2 and its conjugation to azido-functionalized TMB.

FIG. 1 is a schematic structure of the targeted truncated TM, whose amino-acid sequence is encoded by the gene $TM_{GGM}$.

FIG. 2 illustrates results of Western blot analysis of TM derivatives (4-20% SDS-PAGE gel): (1) purified $TM_A$; (2) enterokinase cleavage of $TM_A$ leading to the target protein $TM_B$; (3-5) conjugation of 2 to $TM_B$ over time: 4 h, 8 h and 24 h, respectively. M: Molecular weight marker proteins.

FIG. 5 illustrates a genetically directed synthesis using non-natural amino acids and a conjugation reaction.

DETAILED DESCRIPTION OF THE INVENTION

Figure 3:
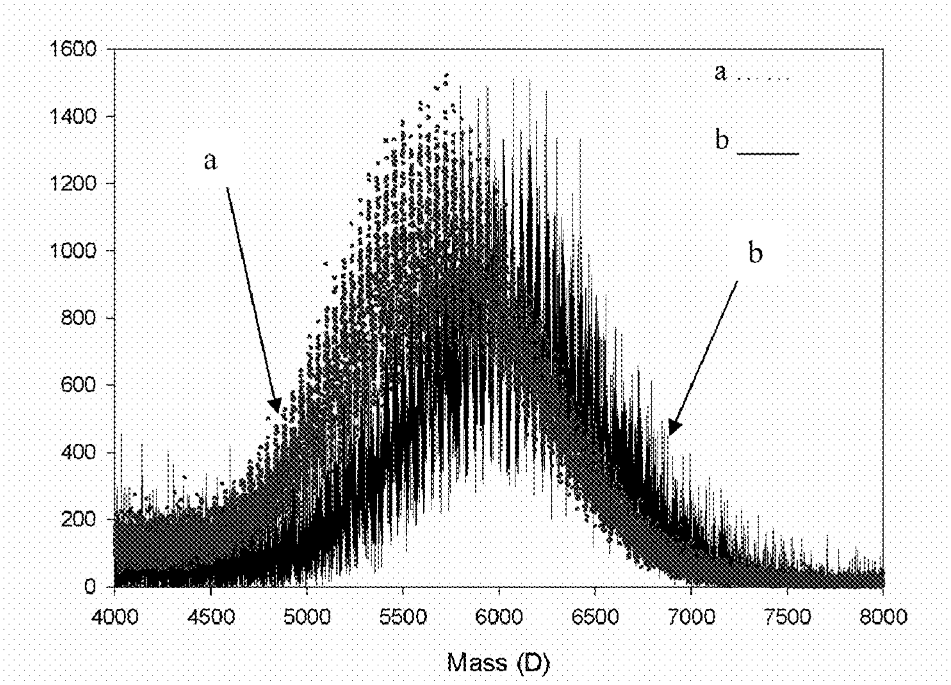
FIG. 3 illustrates MALDI-TOF Mass Spectra of (a) the starting polymer methyl-PEG-amine (average molecular weight detected: 5,668 D) and (b) the methyl-PEG-triarylphosphine conjugate 2 (average molecular weight detected: 6,034 D, calculated 6014 D).

The invention may be further understood by the following non-limiting examples.

Example 1

C-Terminal Site-specific PEGylation of a Truncated Thrombomodulin with Full Bioactivity Abstract: Addition of polyethylene glycol to bioactive proteins (PEGylation) can improve their plasma half-life, enhance stability against proteolytic cleavage, and may also decrease protein immunogenicity. PEGylation can involve reaction to available lysine amino groups, some of which may be within or near a bioactive site. Often PEGylation protocols are nonspecific and result in a loss of protein activity. We disclose a strategy for site-specific PEGylation of a thrombomodulin derivative (TM) at the C-terminus. A truncated TM mutant consisting of epidermal growth factor (EGF)-like domains 4-6 was expressed using recombinant techniques in *Escherichia coli* with a C-terminal azido-methionine. The TM mutant was site-specifically conjugated to a methyl-PEG-triarylphosphine compound via Staudinger reaction. Enzymatic activity of the TM construct before and after PEGylation was substantially similar, which confirms the utility of this site-specific PEGylation method and molecules thereby produced.

Introduction: Pegylation of proteins increases both their molecular size and steric hindrance, which can result in an increase of protein plasma half-life and resistance to proteolytic cleavage. In addition, protein immunogenicity may be decreased (1, 2). Characteristically, PEGylation usually involves reaction to available lysine amino groups, some of which may be within or near a bioactive site. Thus, protocols are often nonspecific and result in a loss of protein activity (3, 4). For example, Han et al. (5) conjugated TM to PEG via trichlorotriazine as a coupling agent for immobilization onto a glass surface. Despite successful immobilization, reduced TM activity was noted presumably due to alteration of protein conformation after PEGylation. To overcome the limitations of current conjugation strategies, several approaches have been proposed. Site-specific PEGylation can be achieved through the introduction of a cysteine residue in engineered proteins with a free thiol available for conjugation reactions (6, 7). As a consequence, several PEG derivatives have been developed for that purpose (8, 9, 10, 11). The efficacy of this approach is compromised, however, by a low yield of PEGylated protein and often by a substantial loss of activity, for example if abnormal protein folding is induced by the introduction of the cysteine residue (12). As an alternative strategy, Yamamoto et al. (13) reported site-specific PEGylation of a lysine-deficient tumor necrosis factor-α at its N-terminus.

We report herein the novel use of a strategy for site-specific PEGylation of human thrombomodulin. This transmembrane protein is a critical regulator of the protein C pathway and represents a major anticoagulant mechanism that is operative under physiologic conditions in vivo (14, 15). TM is a cofactor for thrombin-catalyzed activation of protein C, enhancing the rate of the reaction by 1000-fold (16). In order to closely mimic the TM structure as it appears at the cell surface (17, 18), and consequently preserve its bioactivity, we investigated the PEGylation at the C terminus. Using a genetically-directed synthesis in *Escherichia coli*, we first expressed a short TM construct containing EGF-like domains 4-6 and an azido-functionalized methionine analog (19) as a C-terminal linker. The PEGylation was then achieved through Staudinger ligation (20) with a suitably engineered PEG derivative.

Experimental Procedures

Materials. All chemical reagents were obtained from Sigma Chemical Corporation (St. Louis, Mo.). The methyl-PEG-amine 5,000 was purchased from Netkar Corp. (Hunstville, Ala.). The BamHI and Shrimp Alkaline Phosphatase enzymes were obtained from New England Biolabs, Inc. (Beverly, Mass.). The Quikchange Site-Directed Mutagenesis kit was from Stratagene (La Jolla, Calif.). *E. coli* strain B834 (DE3), plasmid pET-39b(+), S-Tag Rapid Assay kit and Site-Specific Enterokinase Cleavage and Capture Kits were from Novagen (Madison, Wis.). All plasmid purification kits were purchased from QIAGEN Inc. (Chatsworth, Calif.). The mouse monoclonal antibody to human thrombomodulin was from COVANCE Corp. (Richmond, Calif.). Synthetic oligonucleotides were purchased from Integrated DNA Technologies, Inc. (Coralville, Iowa). Purified recombinant human PC and human a thrombin were from Haematologic Technologies Inc. (Essex Junction, Vt.). Human anti-thrombin, recombinant human Thrombomodulin (soluble truncated form of thrombomodulin that lacks the putative transmembrane and the cytoplasmic domains, approximate weight 68 kD) and chromogenic substrate SPECTROZYME PCa were purchased from American Diagnostica Inc. (Stamford, Conn.). All reagents for manipulating DNA and bacteria were sterilized by autoclave.

Instrumentation. MALDI-TOF mass spectrometry data were performed on an Applied Biosystem Voyager-DE™ STR Biospectrometry™ Workstation MALDI-TOF Mass Spectrometer using an 2-(4-hydroxy-phenylazo)benzoic acid matrix. $^{1}$H, $^{13}$C and $^{31}$P NMR spectra were recorded at 600 MHz ($^{1}$H, $^{13}$C) and 242 MHz ($^{31}$P) on a Varian INOVA in $CDCl_3$ (internal $Me_4Si$, δ (delta) ppm). Optical density was recorded on a Varian Cary 50 Bio UV-visible spectrophotometer.

Synthetic Gene Construction. A DNA fragment encoding for EGF (4-6) domains of human TM was obtained by polymerase chain reaction using primers 5'-TACCCTAACTACGACCTGGTG-3' (SEQ ID NO:5) and 5'-TATGAGCAAGCCCGAATG-3' (SEQ ID NO:6). Through a series of intermediate constructs, this fragment was used to generate a gene containing a Leucine (Leu) substitution for Methionine-388 (Met-388), N-terminal and C-terminal BamH I sites and a C-terminal linker GlyGlyMet using site-directed mutagenesis. The final construct ($TM_{GGM}$) was then inserted using the BamH I site of the expression plasmid pET-39b(+). All mutations were verified through sequence analysis.

Protein expression and purification. pET39b(+)-$TM_{GGM}$ was transformed into the *E. coli* methionine auxotroph B834 (DE3). M9 minimal medium (500 mL) supplemented with 1 mM $MgSO_4$, 0.4 wt % glucose, 1 mg/L thiamine chloride, 0.1 mM $CaCl_2$, kanamycin (30 mg/L) and all proteinogenic amino acids (40 mg/L) was inoculated with 20 mL of an overnight culture of the transformed cells. When the turbidity of the culture reached an $OD_{600}$ of 0.8, protein expression was induced by addition of isopropyl-β (beta)-D-thiogalactopyranoside (IPTG) to a final concentration of 0.5 mM. After 5 min, the medium was exchanged to remove methionine, cells were sedimented (4000 g, 20 min), and the cell pellet washed twice with 200 mL of 1×M9 salts. Cells were resuspended in 500 mL of the M9 minimal medium described above, without methionine but supplemented with 100 mg/L of azido-functionalized methionine analog (19). A culture lacking methionine served as the negative control. Cultures were grown for 4.5 h at 37° C.

The expression of the TM protein was analyzed by 4-20% gradient SDS-PAGE gel electrophoresis and visualized by Western blot analysis using a mouse monoclonal antibody to human thrombomodulin. The target protein was expressed as a N-terminal Dsba enzyme fusion to a leader sequence containing an *Enterokinase* cleavage site, hexahistidine, and S-tags (protein $TM_A$). S-Tag Rapid Assay was used to quantify protein concentration and therefore expression yield, which averaged 17 mg/L of cell culture. $TM_A$ was purified from the cell pellet by using immobilized metal-affinity chromatography on TALON TALON™ resin (Clontech Laboratories, Inc.) under native conditions using an imidazole gradient for elution of the target polypeptide. The cells were first harvested by centrifugation at 4° C. at 10,000 g for 30 min and resuspended in 25 mL of lysis buffer (300 mM NaCl, 50 mM $NaH_2PO_4$, 10% glycerol, 1 mg/mL lysozyme, 10 μg/mL PMSF, pH 8). After incubation on ice for 30 min, the cell lysate was clarified by centrifugation at 10,000 g for 20 min. The soluble extract was then loaded onto a column containing TALON™ metal affinity resin (25 mL), which had been pre-equilibrated with lysis buffer. The weakly binding proteins were removed by rinsing the column with 125 mL wash buffer (300 mM NaCl, 50 mM $NaH_2PO_4$, 10% glycerol, 20 mM imidazole, pH 8). $TM_A$ was eluted by the addition of 50 mL of elution buffer (300 mM NaCl, 50 mM $NaH_2PO_4$, 10% glycerol, 250 mM imidazole, pH 8). The chromatographic fractions were analyzed by 4-20% gradient SDS-PAGE gel electrophoresis and visualized by Western blot analysis using mouse monoclonal antibody to human thrombomodulin. The nitrocellulose membrane was developed using the ECL plus Western blotting detection kit (Amersham Biosciences, UK). *Enterokinase* cleavage removed the fusion tag and generated the target protein ($TM_B$). N-terminal sequencing, amino acid compositional and mass analysis (SELDI-TOF) confirmed the integrity of $TM_B$: (Mass detected (m/z): 16,545.2 D (calculated 16,540.1 D)).

Synthesis of methyl-PEG-triarylphosphine (2). 1,3-Dicyclohexylcarbodiimide (DCC) (5.7 mg, 27 μmol) was added to a solution of phosphino reagent (1) (10.3 mg, 28 μmol) in anhydrous $CHCl_3$ (2 mL) at room temperature under argon. The mixture was stirred for 1 h, followed by the addition of methyl-PEG-amine (m-PEG-$NH_2$ ($M_n$ 5 kD)) (120 mg, 24 μmol) dissolved in $CHCl_3$ (2 mL). The mixture was subsequently agitated for 2.5 days under argon. The methyl-PEG-triarylphosphine conjugate was recovered by precipitation in diethyl ether (200 mL) and filtration. The precipitate was dissolved in water. The aqueous solution was filtrated and lyophilized to afford the final product with 50% of substitution. The product was used in the Staudinger reaction without further purification. $^{1}$H NMR (600 MHz, $CDCl_3$): δ 3.38 (s, 3H, O—$CH_3$ (PEG)), 3.45-3.90 (m, 448H, O—$CH_2$ (PEG)), 7.47-7.55 (m, 6H), 7.67-7.70 (m, 5H), 7.91-7.94 (m, 1H), 8.12-8.13 (m, 1H). $^{13}$C NMR (150 MHz, $CDCl_3$): δ 40.0, 41.3, 52.5, 59.3, 70.2, 70.6, 71.1, 72.0, 128.5, 128.7, 128.8, 130.5, 131.0, 131.3, 132.0, 133.3, 134.1, 137.7, 138.1, 166.5, 166.7. $^{31}$P NMR (242 MHz, $CDCl_3$): δ −3.11. MALDI-TOF: 6034 D (calculated 6014 D).

TM-PEG Conjugation. To a solution of $TM_B$ in Phosphate Buffered Saline pH 7.4 (300-500 nM, 100 μL) was added a large excess (1 mg) of lyophilized methyl-PEG-triarylphosphine and the mixture was subsequently heated at 37° C. for 36 h to obtain maximum conjugation. The mixture was divided in half and two sets of reactions were subjected to SDS/PAGE in parallel. Proteins from the first gel were transferred to nitrocellulose membrane and visualized by Western blot analysis using a mouse monoclonal antibody to human thrombomodulin. This procedure monitored the presence of $TM_B$ proteins that had reacted with the phosphine, and were therefore PEG-labeled, as well as unreacted $TM_B$. The second gel was stained with barium chloride/iodine solutions to reveal PEGylated molecules only (21).

TM enzymatic activity assay. A saturated concentration of $TM_B$ in 20 μL of assay buffer (20 mM Tris-HCl pH 7.5, 100 mM NaCl, 2.5 mM $CaCl_2$) was incubated for 30 min at 37° C. with 10 nM human α thrombin and varying amounts of human protein C (0-8 μM). Reactions were quenched by addition of 5 μL of human antithrombin (10.7 μM) and incubation for 5 min at room temperature. The amount of activated protein C formed was determined by addition of 275 μL of SPECTROZYME PCa (218 μM), followed by incubation for 20 min at room temperature. SPECTROZYME PCa is a chromogenic substrate used for the quantification of activated protein C in solution. One mole of the substrate is hydrolyzed by activated protein C producing one mole of p-nitroaniline (pNA). The pNA concentration was determined by UV spectrophotometry at 407 nm using the equation:

$$OD_{407\ nm}=-0.0014+0.0096\ [pNA] \quad (1)$$

where equation (1) was obtained by optical density measurements of pNA solutions of known concentrations. The corresponding rate (mol/min) of p-nitroaniline formed ($R_{pNA}$) was obtained by dividing the pNA concentration by the 20 min assay time.

A second standard plot was used to determine the activated protein C concentration from $R_{pNA}$, where $$R_{pNA}=-0.059+0.0671\ [APC] \quad (2)$$

To obtain equation (2), commercial activated protein C was dissolved in assay buffer at various concentrations and incubated with Spectrozyme PCa for 20 min at room temperature. The corresponding rate (mol/min) of activated protein C formed ($R_{APC}$) by the TM-thrombin complex was obtained by dividing the observed APC concentration by the 30 min assay time.

Values obtained for control experiments without TM were subtracted to give final rates of activated protein C produced. Michaelis-Menten parameters ($k_{cat}$, $K_m$) were calculated from a plot of $R_{APC}$ versus protein C concentration.

Results

Our approach utilized the three consecutive EGF-like domains 4-6 (EGF4-6) of human TM. We analyzed that the corresponding amino-acid sequence contains only one methionine residue (Met-388) and considered its possible impact on protein bioactivity. We also noted that the mutation of Met-388 to leucine (Leu) could contribute resistance to oxidative inactivation while allowing the potential for greater enzymatic activity than the native TM protein. We therefore have made the significant finding that a truncated TM fragment containing EGF domains 4-6 with the insertion of a C-terminal non-natural methionine analog can provide a good target for site-specific PEGylation.

To create a short recombinant bioactive TM mutant, we first used the DNA fragment encoding for the amino-acids sequence 349 to 492 to generate a gene containing a Met-388-Leu substitution and a C-terminal linker GlyGlyMet using site-directed mutagenesis (FIG. 1). The final construct ($TM_{GGM}$) was then inserted in the expression plasmid pET-39b(+). This plasmid contains a leader gene sequence coding for the Dsba enzyme, which is a periplasmic enzyme catalyzing the formation and isomerization of disulfide bonds of expressed proteins. Therefore, we expected the target TM mutant to possess all disulfide bonds required for proper protein folding and enzyme activity. Expression under the induction of IPTG using the *E. coli* methionine auxotroph B834 (DE3)/pET39b(+)-$TM_{GGM}$ in cultures depleted of methionine and supplemented with an azido-functionalized methionine analog, azidohomoalanine (19), afforded the target protein as a N-terminal Dsba enzyme fusion to a leader sequence containing enterokinase recognition sequence, hexahistidine and S-tags. Protein expression was monitored by SDS/PAGE analysis and visualized by Western blot analysis. The target protein was not observed in negative control culture, whereas TM fused to the leader sequence ($TM_A$) was clearly detected in positive control cultures supplemented with azidohomoalanine. The accumulation of $TM_A$ was taken as preliminary evidence for incorporation of the non-natural amino acid. $TM_A$ was purified from the cell pellet by using immobilized metal-affinity chromatography with stepwise imidazole gradient elution under native conditions. Enterokinase cleavage removed the fusion tag and generated the target proteins ($TM_B$). N-terminal sequencing, amino acid compositional and mass analysis (mass detected: 16,545D) confirmed the integrity of $TM_B$. $TM_B$ was characterized by a band at 33 kD on Western blot analysis (FIG. 2), which is consistent with TM associating into dimers even under denaturing conditions (25).

Having expressed an azide-modified form of TM, we then investigated the selective Staudinger ligation of this protein with a methyl-PEG-triarylphosphine conjugate 2 (Scheme A). We choose this ligation protocol in order to minimize the risk of side reactions that might alter TM structure and activity. In its classical form, the Staudinger reaction meets many of the criteria required of a chemoselective ligation in a cellular environment. The phosphine and the azide react rapidly, selectively, and in high yield, in water at room temperature. We used 1 in the synthesis of methyl-PEG-triarylphosphine conjugate 2 (see Kiick et al. (19); preparation of a triarylphosphine compound 1 that was used for the preparation of a protein-Flag conjugate, as well as for labeling cell surface azide-bearing sialic acids with a biotinylated phosphine (20)).

The carboxylic acid group of 1 was reacted with the amino group of a commercially available derivative, methyl-PEG-amine (m-PEG-$NH_2$ (5 kD)) with amide bond formation (Scheme A). The incorporation of a phosphino group in PEG was assessed by $^1H$, $^{13}C$, and $^{31}P$ NMR, as well as by MALDI-TOF spectroscopy (FIG. 3). The average molecular weight of 6,034 D observed for the methyl-PEG-triarylphosphine conjugate 2 is consistent with an expected mass increase of 346 D, as a result of linking the phosphino compound 1 to m-PEG-$NH_2$ (average molecular weight observed: 5,668 D).

Figure 4:
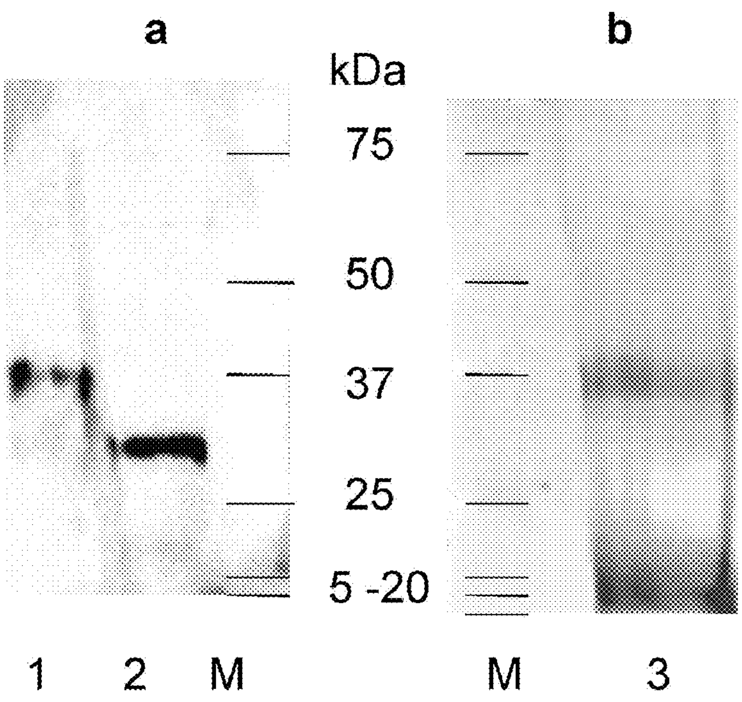
FIG. 4 illustrates (a) Western blot analysis; and (b) barium chloride/iodine staining of a 10% SDS-PAGE gel: (1) and (3) reaction mixture of the bioconjugation of 2 to $TM_B$ after 36 h; (2) initial azido-functionalized $TM_B$. M: Molecular weight marker proteins.

The addition of m-PEG-$NH_2$ to 1 dramatically enhances the water solubility of the hydrophobic phosphino group. A large excess of lyophilized methyl-PEG-triarylphosphine conjugate 2 (1 mg) was added to 100 μL of an aqueous solution of $TM_B$ in PBS at pH 7.4 and Staudinger ligation performed at 37° C. for 24 h. The formation of the $TM_B$-PEG conjugate was followed by Western blot analysis of the reaction mixture over time (FIG. 2). The gel shows a band at higher molecular weight than the initial $TM_B$ with a simultaneous disappearance of the $TM_B$ band. These results indicate that the Staudinger reaction proceeded efficiently with incorporation of the PEG polymer into the TM construct. As the reaction was not complete after 24 h, we allowed it to proceed for an additional 12 h. Western blot analysis (FIG. 4*a*) and barium chloride/iodine staining (FIG. 4*b*) of SDS-PAGE gels were performed in parallel to monitor the formation of the $TM_B$-PEG conjugate. Disappearance of the band characteristic of the unconjugated $TM_B$ revealed that bioconjugation of $TM_B$ to PEG was substantially (approximately 100%) complete. The SDS gel run in parallel under identical conditions but stained with barium chloride/iodine confirmed the presence of PEG in the bioconjugate. The presence of a low molecular weight band represents unreacted methyl-PEG-triarylphosphine 2.

Enzyme activity was assessed to determine the effect of PEGylation on TM cofactor activity (Table 1).

TABLE 1

Michaelis-Menten parameters for protein C activation by TM derivatives.

| Parameter | $TM_A$ | $TM_B$ | PEG-$TM_B$ | Commercial TM |
|---|---|---|---|---|
| $K_M$ (μM) | 0.9 ± 0.2 | 1.0 ± 0.5 | 1.0 ± 0.5 | 0.7 ± 0.1 |
| $k_{cat}$ ($min^{-1}$) | 0.22 ± 0.05 | 0.16 ± 0.05 | 0.20 ± 0.05 | 0.14 ± 0.02 |
| $k_{cat}/K_M$ ($min^{-1} \cdot \mu M^{-1}$) | 0.26 ± 0.10 | 0.16 ± 0.05 | 0.20 ± 0.05 | 0.21 ± 0.05 |

We initially investigated the activity of $TM_A$ and $TM_B$ mutants, as well as a commercial recombinant human TM mutant consisting solely of the extracellular domain (American Diagnostica Inc.). Clarke et al. (23) have reported that the Met-388-Leu mutation results in a 2-fold increase in $k_{cat}$ for the activation of protein C by a thrombin-TM fragment complex. Although we were unable to observe this enhancement of activity, Michaelis-Menten parameters were similar for $TM_A$ and $TM_B$, as well as for the commercial human TM protein. We inferred that the generated TM mutants exhibited the requisite conformation and structure necessary for proper thrombin binding and protein C activation. Significantly, the incorporation of PEG into $TM_B$ did not affect cofactor activity, indicating that this site-specific PEGylation scheme did not interfere with thrombin binding and protein C activation. Parenthetically, despite a concerted effort by our group, previous attempts to generate an enzymatically active truncated TM mutant with a C terminal cysteine, as a potential bioconjugation site, were unsuccessful using both yeast and *E. coli* expression systems. We speculate that an additional terminal cysteine likely interfered with normal protein folding dependent upon the presence of native disulfide loops in the EGF sequences.

CONCLUSIONS

A human thrombomodulin derivative containing EGF(4-6)-like domains designed with an azido-functionalized methionine C-terminal linker was successfully synthesized using a genetic engineering strategy. The protein exhibited bioactivity towards protein C that was comparable to native human TM. The TM construct was successfully conjugated to a novel engineered methyl-PEG-triarylphosphine compound via Staudinger reaction under mild conditions. Enzyme activity before and after PEGylation was substantially similar indicating the utility and successful application of the site-specific PEGylation method. To our knowledge, this report is the first to describe site-specific PEGylation of a thrombomodulin mutant with retention of substantially full bioactivity.

REFERENCES FOR EXAMPLE 1

1. Veronese, F. M. (2001) Peptide and protein PEGylation: a review of problems and solutions. Biomaterials 22, 405-417.
2. Roberts, M. J., Bentley, M. D., and Harris, J. M. (2002) Chemistry for peptide and protein PEGylation. Adv Drug delivery reviews 54, 459-476.
3. Katre, N. V. (1993) The conjugation of proteins with polyethylene glycol and other polymers. Altering properties of proteins to enhance their therapeutic potential. Adv Drug Delivery Rev 10, 91-114.
4. Monkarsh, S. P., Ma, Y. M., Aglione, A., Bailon, P., Ciolek, D., DeBarbieri, B., Graves, M. C., Hollfelder, K., Michel, H., Palleroni, A., Porter, J. E., Russoman, E., Roy, S., and Pan, Y. C. E. (1997) Positional isomers of monopegylated interferon 2a: isolation, characterization, and biological activity. Anal. Biochem. 247, 434-440.
5. Han, H-S., Yang, S-L., Yeh, H-Y., Lin, J-C., Wu, H-L., and Shi, G-Y. (2001) Studies of a novel human thrombomodulin immobilized substrate: surface characterization and anticoagulation activity evaluation. J. Biomater. Sci. Polymer edn. 12, 1075-1089.
6. Tsutsumi, Y., Onda, M., Nagata, S., Lee, B., Kreitman, R. J., and Pastan, I. (2000) Site-specific chemical modification with polyethylene glycol of recombinant immunotoxin anti-Tac(Fv)-PE38 (LMB-2) improves antitumor activity and reduces animal toxicity and immunogenicity. Proc. Natl. Acad. Sci. USA 97, 8548-8553.
7. He, X. H., Shaw, P. C., Xu, L. H., and Tam, S. C. (1999) Site-directed polyethylene glycol modification of trichosanthin: effects on its biological activities, pharmacokinetics, and antigenicity. Life Sci. 64, 1163-1175.
8. Goodson, R. J., and Katre, N. V. (1990) Site-directed pegylation of recombinant interleukin-2 at its glycosylation site. Bio-Technology 8, 343-346.
9. Kogan, T. P. (1992) The synthesis of substituted methoxy-poly(ethylene glycol) derivatives suitable for selective protein modification. Synth. Commun. 22, 2417-2424.
10. Morpurgo, M., Veronese, F. M., Kachensky, D., and Harris, J. M. (1996) Preparation and characterization of poly (ethylene glycol) vinyl sulfone. Bioconjug. Chem. 7, 363-368.
11. Woghiren, C., Sharma, B., and Stein, S. (1993) Protected thiol-polyethylene glycol: a new activated polymer for reversible protein modification. Bioconjug. Chem. 4, 314-318.
12. Kuan, C. T., Wang, Q. C., and Pastan, I. (1994) Pseudomonas exotoxin A mutants. Replacement of surface-exposed residues in domain II with cysteine residues that can be modified with polyethylene glycol in a site-specific manner. J. Biol. Chem. 269, 7610-7616.
13. Yamamoto, Y., Tsutsumi, Y., Yoshioka, Y., Nishibata, T., Kobayashi, K., Okamoto, T., Mukai, Y., Shimizu, T., Nakagawa, S., Nagata, S., and Mayumi, T. (2003) Site-specific PEGylation of a lysine-deficient TNF-alpha with full bioactivity. Nature Biotechnology 21, 546-552.
14. Weiler, H., and Isermann, B. H. Thrombomodulin. (2003) J. Thrombosis and Haemostasis 1, 1515-1524.
15. Kalafatis, M., Egan, J. O., Van't Veer, C., Cawthern, K. M., and Mann, K. G. (1997) The regulation of clotting factors. Crit. Rev. Eukaryot. Gene Expr. 7, 241-280.

16. Esmon, N. L., Owen, W. G., Esmon, C. T. (1982) Isolation of a membrane-boud cofactor for thrombin-catalyzed activation of protein-C. J. Biol. Chem. 257, 859-864.
17. Esmon, C. T. (1992) The regulation of clotting factors. Arteriosclevoris and Thrombosis 12, 135-145.
18. Sadler, J. E. Thrombomodulin structure and function. (1997) Thrombosis and Haemostasis 78, 392-395.
19. Kiick, K. L., Saxon, E., Tirrell, D. A., Bertozzi, C. R. (2002) Incorporation of azides into recombinant proteins for chemoselective modification by the Staudinger ligation. PNAS 99, 19-24.
20. Saxon, E., Bertozzi, C. R. (2000) Cell surface engineering by a modified Staudinger reaction. Science 287, 2007-2010.
21. Kurfurst, M. M. (1992) Detection and molecular weight determination of polyethylene glyol-modified hirudin by staining after sodium dodecyl sulfate-polyacrylamide gel electrophoresis. Anal. Biochem. 200, 244-248.
22. Parkinson, J. F., Nagashima, M. M, Kuhn, I., Leonard, J., Morser, J. (1992) Structure-Function studies of the epidermal growth-factor domains of human thrombomodulin. Biochem Biophys. Res. Commun. 185, 567-576.
23. Clarke, J. H., Light, D. R., Blasko, E. J., Parkinson, F., Nagashima, M., McLean, K., Vilander, L., Andrews, W. H., Morser, J., Glaser, C. B. (1993) The short loop between epidermal growth factor-like domain-4 and domain-5 is critical for human thrombomodulin function. J. Biol. Chem. 268, 6309-6315.
24. Nagashima, M., Lundh, E., Leonard, J. C., Morser, J., Parkinson J. F. (1993) Alanine-scanning mutagenesis of the epidermal growth factor-like domains of human thrombomodulin identifies critical residues for its cofactor activity. J. Biol. Chem. 268, 2888-2892.
25. Glaser, C. B., Morser, J., Clarke, J. H., Blasko, E., McLean, K., Kuhn, I., Chang, R. J., Lin, J.-H., Vilander, L., Andrews, W. H., and Light, D. R. (1992) Oxidation of a specific methionine in thrombomodulin by activated neutrophil products blocks cofactor activity. A potential rapid mechanism for modulation of coagulation. J. Clin. Invest. 90, 2565-2573.

Example 2

Synthesis of a Recombinant Thrombomodulin Conjugate for Immobilization onto a Thin Film Covalent immobilization of TM onto polymeric surfaces has been investigated (AD, AE). In all cases, the conjugation scheme utilized a non-site specific carbodiimide based coupling reaction in which TM was coupled to the substrate via any freely available amino or carboxyl functionality on the protein surface. Consequently, TM bioactivity was often reduced after surface coupling.

We have demonstrated that full length TM can be incorporated into a stable, membrane-mimetic thin film over a wide range of surface concentrations by a process of lipid/protein self-assembly and in situ photopolymerization. See AA, AB, AC. However, as an alternate strategy using genetically directed synthesis, we have created a short TM construct containing the catalytic region of EGF domains 4-6 along with an artificial amino acid analog, azido (N3)-alanine, incorporated biosynthetically at the C-terminus of the protein (rTM-N3). Through Staudinger ligation with a suitable phosphine PEO derivative (MW 3000), we have generated TM-PEO conjugates. The azidoTM construct and conjugate have been fully characterized by Western blotting and SDSPAGE. The catalytic activity (kcat, Km) of the conjugate is comparable to the rTM-N3 mutant alone, as well as a commercially available soluble human TM protein (Solulin™). Of note, by using a biotin or diene terminated PEG derivative, for example, TM can then be rapidly and directly coupled to a surface, which provides an additional approach for linking TM to membrane assemblies.

Figure 6:
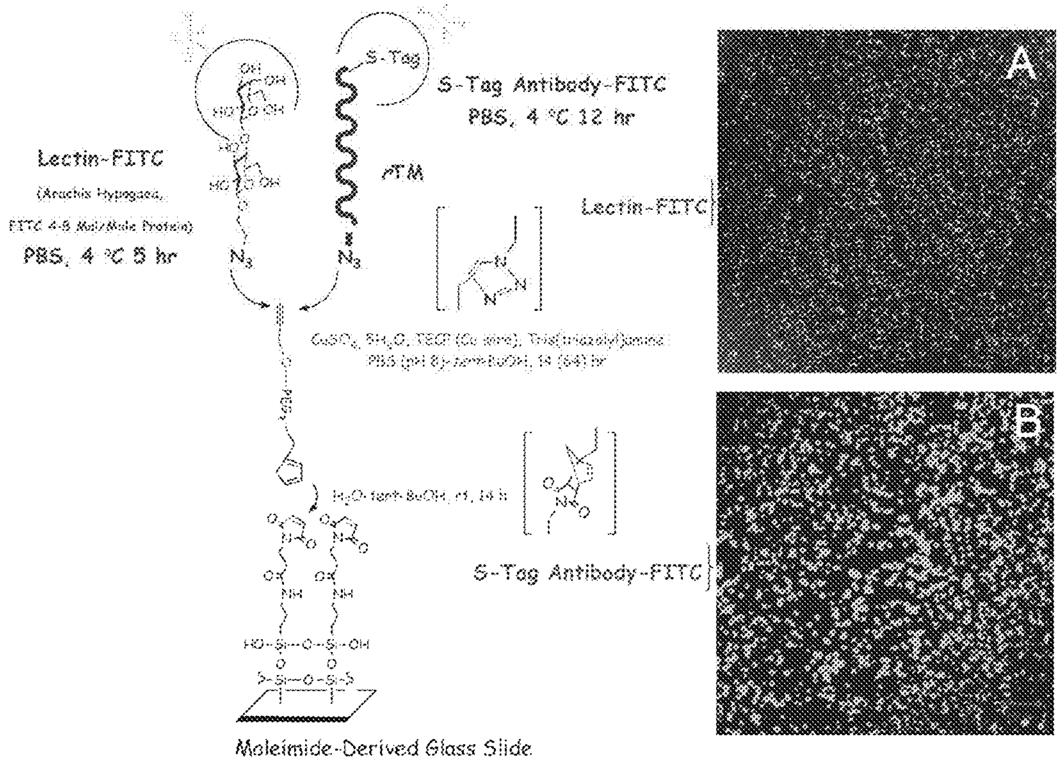
FIG. 6 illustrates bioorthogonal surface ligation of azidolactose (A) and azidoTM (B) via azide-alkyne [3+2] cycloaddition ("Click" chemistry). Surface bound carbohydrates and TM were visualized by staining with a FITC-lectin (A) and FITC anti-S-tag MAb (B), respectively.

Staudinger ligation of azidoTM with phosphine-PEO is not without limitations. The requisite phosphines are susceptible to air oxidation, and their optimization for improved water solubility and increased reaction rate is synthetically challenging. Thus, we have investigated alternate strategies for direct single-step bioorthogonal coupling of rTM-N3 to target surfaces. Specifically, we have demonstrated that rTM-N3 can be coupled to surfaces via an azide-alkyne [3+2] cycloaddition, termed "click" chemistry (AF, AG). Significantly, both this approach and Staudinger ligation provide a means to selectively conjugate complex biomolecules in richly functionalized environs under mild conditions that do not alter biomolecular activity. The chemical conjugation scheme is summarized in FIG. 6. See (AF).

The rTM-N3 was expressed with an N-terminal S-tag, which allowed the effectiveness of surface coupling to be evaluated using a FITC-labeled anti-S-tag antibody. Likewise, the feasibility of using this strategy to link N3-derivatized carbohydrates to target surfaces was also evaluated using azidolactose, as a model oligosaccharide for more complex polysaccharides, such as heparin. A FITC-labeled lectin was used to ascertain the extent and homogeneity of carbohydrate surface conjugation. This scheme proved quite versatile for surface coupling of both rTM and carbohydrates.

REFERENCES FOR EXAMPLE 2

AA. Cazalis C S, Haller C A, Chaikof E L. Site-specific pegylation of a truncated thrombomodulin derivative. Polymer Mater Sci Eng 2004; 227:198-9.
AB. Cazalis C S, Haller C A, Sease-Cargo L, Chaikof E L. C-terminal site-specific pegylation of a truncated thrombomodulin mutant with retention of full bioactivity. Bioconjugate Chem 2004; 15:1005-9.
AC. Cazalis C S, Haller C A, Sease-Cargo L, Chaikof E L. Thrombomodulin conjugates. USA. PCT 60/546,436, Feb. 20, 2004.
AD. Kishida A, Akatsuka Y, Yanagi M, Aikou T, Maruyama I, Akashi M. In vivo and ex vivo evaluation of the antithrombogenicity of human thrombomodulin immobilized biomaterials. ASAIO Journal 1995; 41(3):M369-74.
AE. Vasilets V N, Hermel G, Konig U, Werner C, Muller M, Simon F, et al. Microwave CO2 plasma-initiated vapour phase graft polymerization of acrylic acid onto polytetrafluoroethylene for immobilization of human thrombomodulin. Biomaterials 1997; 18(17):1139-45.
AF. Wang Q, Chan T R, Hilgraf R, Fokin W, Sharpless K B, Finn M G. Bioconjugation by Copper(I)-Catalyzed Azide-Alkyne [3+2] Cycloaddition. J Am Chem Soc 2003; 125 (11):3192-3193.
AG. Agard N J, Prescher J A, Bertozzi C R. A strain-promoted [3+2] azide-alkyne cycloaddition for covalent modification of biomolecules in living systems. J Am Chem Soc 2004; 126(46):15046-15047.

STATEMENT REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Compositions including compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. A biomolecule such as a precursor protein or precursor nucleic acid can be a prodrug. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation. The scope of the invention shall be limited only by the claims.

REFERENCES

Wood M J et al., NMR Structures Reveal How Oxidation Inactivates Thrombomodulin, Biochemistry 2003, 42, 11932-11942.

U.S. Pat. No. 5,126,140, Thrombomodulin-coated biocompatible substance; U.S. Pat. No. 5,834,028, Soluble thrombomodulin-containing composition; U.S. Pat. No. 5,863, 760, Protease-resistant thrombomodulin analogs; U.S. Pat. No. 5,583,102, Human thrombomodulin in wound healing; U.S. Pat. No. 6,632,791, Thrombomodulin analogs for pharmaceutical use; U.S. Pat. No. 5,256,770, Oxidation resistant thrombomodulin analogs; U.S. Pat. No. 5,108, 759, Endothelial envelopment drug carriers; U.S. Pat. No. 6,410,057, Biodegradable mixed polymeric micelles for drug delivery.

Weiler, H., lsermann, B. H. Thrombomodulin. (2003) J. Thrombosis and Haemostasis 1, 1515-1524.

Kalafatis, M., Egan, J. O., Van't Veer, C., Cawthern, K. M., Mann, K. G. (1997) The regulation of clotting factors. Crit. Rev. Eukaryot. Gene Expr. 7, 241-280.

Esmon, N. L., Owen, W. G., Esmon, C. T. (1982) Isolation of a membrane-boud cofactor for thrombin-catalyzed activation of protein-C. J. Biol. Chem. 257, 859-864.

Esmon, C. T. (1992) The regulation of clotting factors. Arteriosclevoris and Thrombosis 12, 135-145.

Parkinson, J. F., Nagashima, M. M, Kuhn, I., Leonard, J., Morser, J. (1992) Structure-Function studies of the epidermal growth-factor domains of human thrombomodulin. Biochem Biophys. Res. Commun. 185, 567-576.

Clarke, J. H., Light, D. R., Blasko, E. J., Parkinson, F., Nagashima, M., McLean, K., Vilander, L., Andrews, W. H., Morser, J., Glaser, C. B. (1993) The short loop between epidermal growth factor-like domain-4 and domain-5 is critical for human thrombomodulin function. J. Biol. Chem. 268, 6309-6315.

Nagashima, M., Lundh, E., Leonard, J. C., Morser, J., Parkinson J. F. (1993) Alanine-scanning mutagenesis of the epidermal growth factor-like domains of human thrombomodulin identifies critical residues for its cofactor activity. J. Biol. Chem. 268, 2888-2892.

Glaser, C. B., Morser, J., Clarke, J. H., blasko, E., McLean, K., Kuhn, I., Chang, R.-J., Lin, J.-H., Vilander, L., Andrews, W. H., and Light, D. R. (1992) Oxidation of a secific methionine in thrombomodulin by activated neutrophil products blocks cofactor activity-a potential rapid mechanism for modulation of coagulation. Clin. Invest. 90, 2565-2573.

Kiick, K. L., Saxon, E., Tirrell, D. A., Bertozzi, C. R. (2002) Incorporation of azides into recombinant proteins for chemoselective modification by the Staudinger ligation. PNAS 99, 19-24.

Saxon, E., Bertozzi, C. R. (2000) Cell surface engineering by a modified Staudinger reaction. Science 287, 2007-2010.

Veronese, F. M. (2001) Peptide and protein PEGylation: a review of problems and solutions. Biomaterials 22, 405-417.

Roberts, M. J., Bentley, M. D., Harris, J. M. (2002) Chemistry for peptide and protein PEGylation. Adv Drug delivery reviews 54, 459-476.

Katre, N. V. (1993) The conjugation of proteins with polyethylene glycol and other polymers. Altering properties of proteins to enhance their therapeutic potential. Adv Drug Delivery Rev 10, 91-114.

Monkarsh, S. P., Ma, Y. M., Aglione, A., Bailon, P., Ciolek, D., DeBarbieri, B., Graves, M. C., Hollfelder, K., Michel, H., Palleroni, A., Porter, J. E., Russoman, E., Roy, S., Pan, Y. C. E. (1997) Positional isomers of monopegylated interferon 2a: isolation, characterization, and biological activity. Anal. Biochem. 247, 434-440.

Han, H.-S., Yang, S.-L., Yeh, H.-Y., Lin, J.-C., Wu, H.-L., Shi, G.-Y. (2001) Studies of a novel human thrombomodulin immobilized substrate: surface characterization and anticoagulation activity evaluation. J. Biomater. Sci. Polymer edn, 12, 1075-1089.

Tsutsumi, Y., Onda, M., Nagata, S., Lee, B., Kreitman, R. J., Pastan, I. (2000) Site-specific chemical modification with polyethylene glycol of recombinant immunotoxin anti-Tac (Fv)-PE38 (LMB-2) improves antitumor activity and reduces animal toxicity and immunogenicity. Proc. Natl. Acad. Sci. USA 97, 8548-8553.

He, X. H., Shaw, P. C., Xu, L. H., Tam, S. C. (1999) Site-directed polyethylene glycol modification of trichosanthin: effects on its biological activities, pharmacokinetics, and antigenicity. Life Sci. 64, 1163-1175.

Goodson, R. J., Katre, N. V. (1990) Site-directed pegylation of recombinant interleukin-2 at its glycosylation site. Biotechnology 8, 343-346.

Kogan, T. P. (1992) The synthesis of substituted methoxy-poly(ethylene glycol) derivatives suitable for selective protein modification. Synth. Commun. 22, 2417-2424.

Morpurgo, M., Veronese, F. M., Kachensky, D., Harris, J. M. (1996) Preparation and characterization of poly(ethylene glycol) vinyl sulfone. Bioconjug. Chem. 7, 363-368.

Woghiren, C., Sharma, B., Stein, S. (1993) Protected thiol-polyethylene glycol: a new activated polymer for reversible protein modification. Bioconjug. Chem. 4, 314-318.

Karpusas, M., Nolte, M., Benton, C. B., Meier, W., Lipscomb, W. N., Goelz, S. (1997) The crystal structure of human interferon beta at 2.2-A resolution. Proc. Natl. Acad. Sci. USA 94, 11813-11818.

Kuan, C. T., Wang, Q. C., Pastan, I. (1994) Pseudomonas exotoxin A mutants. Replacement of surface-exposed residues in domain II with cysteine residues that can be modified with polyethylene glycol in a site-specific manner. J. Biol. Chem. 269, 7610-7616.

Yamamoto, Y., Tsutsumi, Y., Yoshioka, Y., Nishibata, T., Kobayashi, K., Okamoto, T., Mukai, Y., Shimizu, T., Nakagawa, S., Nagata, S., Mayumi, T. (2003) Site-specific PEGylation of a lysine-deficient TNF-alpha with full bioactivity. Nature Biotechnology 21, 546-552.

Kurfurst, M. M. (1992) Detection and molecular weight determination of polyethylene glyol-modified hirudin by staining after sodium dodecyl sulfate-polyacrylamide gel electrophoresis. Anal. Biochem. 200, 244-248.

Manjula, B. N., Tsai, A., Upadhya, R., Perumalsamy, K., Smith, P. K., Malavalli, A., Vandegriff, K., Winslow, R. M., Intaglietta, M., Prabhakaran, M., Friedman, J. M., Acharya, A. S. (2003) Site-specific PEGylation of hemoglobin at cys-93(beta): Correlation between the colligative properties of the PEGylated protein and the length of the conjugated PEG chain. Bioconjugate Chemistry 14, 464-472.

Feng, J., Tseng, P.-Y., Faucher, K. M., Orban, J. M., Sun, X.-L., Chaikof, E. L. (2002) Functional reconstitution of thrombomodulin within a substrate-supported membrane-mimetic polymer film. Langmuir 18, 9907-9913.

Kishida, A., Ueno, Y., Maruyama, I., Akashi, M. (1994) Immobilization of human thrombomodulin on biomaterials-Evaluation of the activity of immobilized human thrombomodulin. Biomaterials 15, 1170-1174.

Kishida, A., Ueno, Y., Maruyama, I., Akashi, M. (1994) Immobilization of human thrombomodulin on onto poly (ether urethane urea) for developing antithrombogenic blood-contacting materials. Biomaterials 15, 848-852.

The invention claimed is:

1. A conjugate comprising a recombinant human thrombomodulin protein and a polymer, wherein the recombinant human thrombomodulin protein comprises epidermal growth factor (EGF)-like domains (4-6), a substitution of a leucine for a methionine at amino acid position 40 of SEQ ID NO:3 and a GGM amino acid motif appended at a carboxy terminus of said recombinant human thrombomodulin protein, wherein said recombinant human thrombomodulin protein comprises the amino acid sequence of SEQ ID NO:3 and wherein the polymer is selected from the group consisting of polyethylene glycol, poly(t-butyl acrylate), poly (t-butyl methacrylate), polyacrylamide, poly(arginine), glycolipid, glycoprotein and polysaccharide.

2. The conjugate of claim 1, wherein the polymer is polyethylene glycol.

3. A conjugate comprising a recombinant human thrombomodulin protein and a polymer, wherein the recombinant human thrombomodulin protein comprises the amino acid sequence of SEQ ID NO:3 and wherein the polymer is selected from the group consisting of polyethylene glycol, poly(t-butyl acrylate), poly(t-butyl methacrylate), polyacrylamide, poly(arginine), glycolipid, glycoprotein and polysaccharide.

4. The conjugate of claim 3, wherein the polymer is polyethylene glycol.

5. The conjugate of claim 3, wherein the conjugate is soluble.

6. The conjugate of claim 3, wherein the polymer is a linear, branched or synthetic polymer.

7. A recombinant human thrombomodulin protein comprising the amino acid sequence of SEQ ID NO:3.

* * * * *